(12) United States Patent
Meade et al.

(10) Patent No.: US 9,717,493 B1
(45) Date of Patent: *Aug. 1, 2017

(54) DEVICES AND METHODS FOR SURGICAL SUTURING

(71) Applicant: EndoEvolution, LLC, Raynham, MA (US)

(72) Inventors: John C. Meade, Mendon, MA (US); Niall G. Deloughry, Lemerick (IE); Gerald I. Brecher, North Andover, MA (US); James H. Bleck, Chelmsford, MA (US)

(73) Assignee: ENDOEVOLUTION, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/490,539

(22) Filed: Apr. 18, 2017

Related U.S. Application Data

(60) Continuation of application No. 15/260,094, filed on Sep. 8, 2016, now Pat. No. 9,649,107, which is a (Continued)

(51) Int. Cl.
*A61B 17/04* (2006.01)
*A61B 17/06* (2006.01)
(Continued)

(52) U.S. Cl.
CPC ...... *A61B 17/0469* (2013.01); *A61B 17/0482* (2013.01); *A61B 17/0491* (2013.01);
(Continued)

(58) Field of Classification Search
CPC ............ A61B 17/0469; A61B 17/0625; A61B 17/062; A61B 17/06109; A61B 17/06066; A61B 17/06004; A61B 17/0482
See application file for complete search history.

(56) References Cited

U.S. PATENT DOCUMENTS

| | | |
|---|---|---|
| 1,327,577 A | 1/1920 | Turner |
| 1,822,330 A | 9/1931 | Ainslie |

(Continued)

FOREIGN PATENT DOCUMENTS

| | | |
|---|---|---|
| CN | 2169381 | 6/1994 |
| CN | 201082170 | 7/2008 |

(Continued)

OTHER PUBLICATIONS

International Preliminary Report on Patentability dated Jan. 13, 2008 and Written Opinion dated Jun. 13, 2008 for PCT/US05/33507.

(Continued)

*Primary Examiner* — Tuan V Nguyen
(74) *Attorney, Agent, or Firm* — Crawford Maunu PLLC

(57) ABSTRACT

An apparatus and a method for surgical suturing with thread management. An illustrative apparatus for tissue suturing includes a cartridge having a suturing needle having a pointed end and a blunt end, the suturing needle capable of rotating about an axis, a reciprocating needle drive, and an actuator capable of releasably engaging the needle drive to rotate the needle. A method for suturing tissue is provided that includes placing a suturing device having a cartridge containing a suturing needle to span at least one tissue segment, activating an actuator to cause rotational movement of the suturing needle through the at least one tissue segment, and deactivating the actuator to stop an advancing movement of the suturing needle to cause a suturing material to be pulled through the at least one tissue segment forming a stitch.

32 Claims, 18 Drawing Sheets

Related U.S. Application Data continuation of application No. 13/197,870, filed on Aug. 4, 2011, now Pat. No. 9,445,807, which is a continuation of application No. 11/387,127, filed on Mar. 22, 2006, now Pat. No. 8,066,737, which is a division of application No. 11/121,810, filed on May 4, 2005, now abandoned, which is a division of application No. 10/127,254, filed on Apr. 22, 2002, now Pat. No. 6,923,819.

(60) Provisional application No. 60/298,281, filed on Jun. 14, 2001.

(51) Int. Cl.
*A61B 17/062* (2006.01)
*A61B 17/11* (2006.01)
*A61B 17/29* (2006.01)

(52) U.S. Cl.
CPC .... *A61B 17/06004* (2013.01); *A61B 17/0625* (2013.01); *A61B 17/06066* (2013.01); *A61B 17/06114* (2013.01); *A61B 17/1114* (2013.01); *A61B 2017/06019* (2013.01); *A61B 2017/06028* (2013.01); *A61B 2017/06071* (2013.01); *A61B 2017/2927* (2013.01)

(56) References Cited

U.S. PATENT DOCUMENTS

| | | |
|---|---|---|
| 2,327,353 A | 8/1943 | Karle |
| 2,601,564 A | 6/1952 | Smith |
| 3,197,997 A | 8/1965 | Kurtz |
| 3,311,110 A | 3/1967 | Singerman et al. |
| 3,344,790 A | 10/1967 | Dorner |
| 3,762,418 A | 10/1973 | Wasson |
| 3,834,599 A | 9/1974 | Herr |
| 3,835,912 A | 9/1974 | Kristensen et al. |
| 3,910,282 A | 10/1975 | Messer et al. |
| 3,951,261 A | 4/1976 | Mandel et al. |
| 3,972,418 A | 8/1976 | Schuler et al. |
| 4,027,608 A | 6/1977 | Arbuckle |
| 4,235,177 A | 11/1980 | Arbuckle |
| 4,327,655 A | 5/1982 | Addy et al. |
| 4,331,277 A | 5/1982 | Green |
| 4,437,465 A | 3/1984 | Nomoto et al. |
| 4,509,945 A | 4/1985 | Kramann et al. |
| 4,527,564 A | 7/1985 | Eguchi et al. |
| 4,557,265 A | 12/1985 | Andersson |
| 4,621,640 A | 11/1986 | Mulhollan et al. |
| 4,841,888 A | 6/1989 | Mills et al. |
| 4,899,746 A | 2/1990 | Brunk |
| 4,957,502 A | 9/1990 | Takase |
| 5,080,663 A | 1/1992 | Mills et al. |
| 5,089,012 A | 2/1992 | Prou |
| 5,201,760 A | 4/1993 | West |
| 5,210,376 A | 5/1993 | Caviar |
| 5,269,806 A | 12/1993 | Sardelis et al. |
| 5,305,281 A | 4/1994 | Lubeck |
| 5,306,281 A | 4/1994 | Beurrier |
| 5,308,353 A | 5/1994 | Beurrier |
| 5,318,578 A | 6/1994 | Hasson |
| 5,344,061 A | 9/1994 | Crainich |
| 5,358,498 A | 10/1994 | Shave |
| 5,364,408 A | 11/1994 | Gordon |
| 5,373,101 A | 12/1994 | Barabolak |
| 5,376,101 A | 12/1994 | Green et al. |
| 5,387,221 A | 2/1995 | Bisgaard |
| 5,437,681 A | 8/1995 | Meade et al. |
| 5,462,558 A | 10/1995 | Kolesa et al. |
| 5,472,081 A | 12/1995 | Kilgrow et al. |
| 5,474,568 A | 12/1995 | Scott |
| 5,478,344 A | 12/1995 | Stone et al. |
| 5,478,345 A | 12/1995 | Stone et al. |
| 5,480,409 A | 1/1996 | Riza |
| 5,503,266 A | 4/1996 | Kalbfeld et al. |
| 5,514,159 A | 5/1996 | Matula et al. |
| 5,540,705 A | 7/1996 | Meade et al. |
| 5,571,119 A | 11/1996 | Atala |
| 5,575,800 A | 11/1996 | Gordon |
| 5,578,044 A | 11/1996 | Gordon et al. |
| 5,643,295 A | 7/1997 | Yoon |
| 5,645,552 A | 7/1997 | Sherts |
| 5,665,096 A | 9/1997 | Yoon |
| 5,665,109 A | 9/1997 | Yoon |
| 5,669,490 A | 9/1997 | Colligan et al. |
| 5,675,961 A | 10/1997 | Cerwin et al. |
| 5,709,693 A | 1/1998 | Taylor |
| 5,713,910 A | 2/1998 | Gordon et al. |
| 5,715,942 A | 2/1998 | Li et al. |
| 5,741,277 A | 4/1998 | Gordon et al. |
| 5,755,729 A | 5/1998 | de la Torre et al. |
| 5,759,188 A | 6/1998 | Yoon |
| 5,766,186 A | 6/1998 | Faraz et al. |
| 5,814,069 A | 9/1998 | Schulze et al. |
| 5,814,071 A | 9/1998 | McDevitt et al. |
| 5,833,695 A | 11/1998 | Yoon |
| 5,860,992 A | 1/1999 | Daniel et al. |
| 5,891,160 A | 4/1999 | Williamson, IV et al. |
| 5,906,273 A | 5/1999 | Pohle et al. |
| 5,908,426 A | 6/1999 | Pierce |
| 5,908,428 A | 6/1999 | Scirica et al. |
| 5,911,727 A | 6/1999 | Taylor |
| 5,954,733 A | 9/1999 | Yoon |
| 5,968,077 A | 10/1999 | Wojciechowicz et al. |
| 5,993,466 A | 11/1999 | Yoon |
| 6,016,905 A | 1/2000 | Gemma et al. |
| 6,036,694 A | 3/2000 | Goble et al. |
| 6,048,351 A | 4/2000 | Gordon et al. |
| 6,053,908 A | 4/2000 | Crainich et al. |
| 6,056,771 A | 5/2000 | Proto |
| 6,071,289 A | 6/2000 | Stefanchik et al. |
| 6,096,051 A | 8/2000 | Kortenbach et al. |
| 6,126,666 A | 10/2000 | Trapp et al. |
| 6,135,385 A | 10/2000 | Martinez de Lahidalga |
| 6,136,010 A | 10/2000 | Modesitt et al. |
| 6,159,224 A | 12/2000 | Yoon |
| 6,261,307 B1 | 7/2001 | Yoon et al. |
| 6,270,508 B1 | 8/2001 | Klieman et al. |
| 6,322,581 B1 | 11/2001 | Fukuda et al. |
| 6,332,888 B1 | 12/2001 | Levy et al. |
| 6,346,111 B1 | 2/2002 | Gordon et al. |
| 6,443,962 B1 | 9/2002 | Gaber |
| 6,454,777 B1 | 9/2002 | Green |
| 6,454,778 B2 | 9/2002 | Kortenbach |
| 6,494,888 B1 | 12/2002 | Laufer et al. |
| 6,506,196 B1 | 1/2003 | Laufer |
| 6,558,400 B2 | 5/2003 | Deem et al. |
| 6,656,194 B1 | 12/2003 | Gannoe et al. |
| 6,663,639 B1 | 12/2003 | Laufer et al. |
| 6,719,763 B2 | 4/2004 | Chung et al. |
| 6,719,764 B1 | 4/2004 | Gellman et al. |
| 6,746,460 B2 | 6/2004 | Gannoe et al. |
| 6,755,843 B2 | 6/2004 | Chung et al. |
| 6,835,200 B2 | 12/2004 | Laufer et al. |
| 6,877,352 B1 | 4/2005 | Schlereth |
| 6,908,427 B2 | 6/2005 | Fleener et al. |
| 6,923,819 B2 | 8/2005 | Meade et al. |
| 6,955,643 B2 | 10/2005 | Gellman et al. |
| 7,004,951 B2 | 2/2006 | Gibbens, III |
| 7,033,370 B2 | 4/2006 | Gordon et al. |
| 7,041,111 B2 | 5/2006 | Chu |
| 7,144,401 B2 | 12/2006 | Yamamoto et al. |
| 7,166,116 B2 | 1/2007 | Lizardi et al. |
| 7,338,504 B2 | 3/2008 | Gibbens et al. |
| 7,615,060 B2 | 11/2009 | Stokes et al. |
| 7,628,796 B2 | 12/2009 | Shelton, IV et al. |
| 7,637,909 B2 | 12/2009 | Lechot et al. |
| 7,766,925 B2 | 8/2010 | Stokes et al. |
| 7,828,812 B2 | 11/2010 | Stokes et al. |
| 7,833,236 B2 | 11/2010 | Stokes et al. |
| 7,846,169 B2 | 12/2010 | Shelton, IV et al. |
| 7,862,572 B2 | 1/2011 | Meade et al. |
| 7,887,554 B2 | 2/2011 | Stokes et al. |

(56) References Cited

U.S. PATENT DOCUMENTS

| | | |
|---|---|---|
| 7,976,533 B2 | 7/2011 | Larsson |
| 7,976,555 B2 | 7/2011 | Meade et al. |
| 7,993,354 B1 | 8/2011 | Brecher et al. |
| 8,066,737 B2 | 11/2011 | Meade et al. |
| 8,123,764 B2 | 2/2012 | Meade et al. |
| 8,469,973 B2 | 6/2013 | Meade et al. |
| 8,500,756 B2 | 8/2013 | Papa et al. |
| 8,623,048 B2 | 1/2014 | Brecher et al. |
| 8,641,728 B2 | 2/2014 | Stokes et al. |
| 8,702,732 B2 | 4/2014 | Woodard, Jr. et al. |
| 8,906,043 B2 | 12/2014 | Woodard, Jr. et al. |
| 9,125,645 B1 | 9/2015 | Martin et al. |
| 9,173,655 B2 | 11/2015 | Martin |
| 9,220,496 B2 | 12/2015 | Martin et al. |
| 9,357,998 B2 | 6/2016 | Martin et al. |
| 9,370,354 B1 | 6/2016 | Martin et al. |
| 9,375,212 B2 | 6/2016 | Martin et al. |
| 9,398,905 B2 | 7/2016 | Martin |
| 9,427,226 B2 | 8/2016 | Martin et al. |
| 9,427,227 B2 | 8/2016 | Martin et al. |
| 9,445,807 B2 | 9/2016 | Brecher et al. |
| 9,451,948 B2 | 9/2016 | Meade et al. |
| 9,474,522 B2 | 10/2016 | Deck et al. |
| 9,474,523 B2 | 10/2016 | Meade et al. |
| 9,486,209 B2 | 11/2016 | Martin et al. |
| 9,498,207 B2 | 11/2016 | Martin et al. |
| 9,526,495 B2 | 12/2016 | Martin et al. |
| 2002/0107530 A1 | 8/2002 | Sauer et al. |
| 2002/0116011 A1 | 8/2002 | Chee Chung et al. |
| 2002/0173800 A1 | 11/2002 | Dreyfuss et al. |
| 2002/0193809 A1 | 12/2002 | Meade et al. |
| 2002/0198542 A1 | 12/2002 | Yamamoto et al. |
| 2003/0083674 A1 | 5/2003 | Gibbens |
| 2003/0105475 A1 | 6/2003 | Sancoff et al. |
| 2003/0171760 A1 | 9/2003 | Gambale |
| 2003/0181924 A1 | 9/2003 | Yamamoto et al. |
| 2003/0233104 A1 | 12/2003 | Gellman et al. |
| 2003/0233108 A1 | 12/2003 | Gellman et al. |
| 2004/0034369 A1 | 2/2004 | Sauer et al. |
| 2004/0034372 A1 | 2/2004 | Chu |
| 2004/0044354 A1 | 3/2004 | Gannoe et al. |
| 2004/0059350 A1 | 3/2004 | Gordon et al. |
| 2004/0082963 A1 | 4/2004 | Gannoe et al. |
| 2004/0088008 A1 | 5/2004 | Gannoe et al. |
| 2004/0122473 A1 | 6/2004 | Ewers et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2005/0015101 A1 | 1/2005 | Gibbens et al. |
| 2005/0035007 A1 | 2/2005 | Kennedy et al. |
| 2005/0055038 A1 | 3/2005 | Kelleher et al. |
| 2005/0070931 A1 | 3/2005 | Li et al. |
| 2005/0075653 A1 | 4/2005 | Saadat et al. |
| 2005/0262984 A1 | 12/2005 | Hetcher et al. |
| 2006/0069396 A1 | 3/2006 | Meade et al. |
| 2006/0111732 A1 | 5/2006 | Gibbens et al. |
| 2006/0224184 A1 | 10/2006 | Stefanchik et al. |
| 2006/0282089 A1 | 12/2006 | Stokes et al. |
| 2006/0282090 A1 | 12/2006 | Stokes et al. |
| 2006/0282091 A1 | 12/2006 | Shelton et al. |
| 2006/0282092 A1 | 12/2006 | Stokes et al. |
| 2006/0282093 A1 | 12/2006 | Shelton et al. |
| 2006/0282094 A1 | 12/2006 | Stokes et al. |
| 2006/0282095 A1 | 12/2006 | Stokes et al. |
| 2006/0282096 A1 | 12/2006 | Papa et al. |
| 2006/0282097 A1 | 12/2006 | Ortiz et al. |
| 2006/0282098 A1 | 12/2006 | Shelton et al. |
| 2006/0282099 A1 | 12/2006 | Stokes et al. |
| 2007/0135838 A1 | 6/2007 | Meyer |
| 2008/0132919 A1 | 6/2008 | Chui et al. |
| 2008/0140091 A1 | 6/2008 | DeDeyne et al. |
| 2009/0024145 A1 | 1/2009 | Meade et al. |
| 2010/0036415 A1 | 2/2010 | Cabezas |
| 2010/0049219 A1 | 2/2010 | Cronin et al. |
| 2010/0130990 A1 | 5/2010 | Saliman |
| 2010/0152751 A1 | 6/2010 | Meade et al. |
| 2014/0171977 A1 | 6/2014 | Martin et al. |
| 2014/0171979 A1 | 6/2014 | Martin et al. |
| 2014/0172015 A1 | 6/2014 | Martin et al. |
| 2015/0133967 A1 | 5/2015 | Martin |
| 2015/0351745 A1 | 12/2015 | Mumaw et al. |
| 2015/0351746 A1 | 12/2015 | Martin et al. |
| 2015/0351749 A1 | 12/2015 | Martin et al. |
| 2015/0351756 A1 | 12/2015 | Martin et al. |
| 2016/0317148 A1 | 11/2016 | Martinez |
| 2016/0331374 A1 | 11/2016 | Martin et al. |
| 2016/0345958 A1 | 12/2016 | Martin et al. |
| 2016/0346827 A1 | 12/2016 | Martin et al. |
| 2016/0361055 A1 | 12/2016 | Martin et al. |
| 2016/0367238 A1 | 12/2016 | Deck et al. |
| 2016/0367239 A1 | 12/2016 | Mumaw et al. |
| 2016/0367240 A1 | 12/2016 | Shelton, IV et al. |
| 2016/0367243 A1 | 12/2016 | Martin et al. |

FOREIGN PATENT DOCUMENTS

| | | |
|---|---|---|
| DE | 4310315 | 10/1993 |
| EP | 0648474 | 4/1995 |
| EP | 2103262 | 9/2009 |
| EP | 2292157 | 3/2011 |
| EP | 2308391 | 4/2011 |
| EP | 2370002 | 10/2011 |
| EP | 1791476 | 12/2015 |
| FR | 2540377 | 8/1984 |
| GB | 18602 | 0/1908 |
| JP | 55151956 | 11/1980 |
| JP | 07178100 | 7/1995 |
| JP | 07328021 | 12/1995 |
| JP | H11276492 | 10/1999 |
| JP | 2000139931 | 5/2000 |
| JP | 2005253987 | 9/2005 |
| WO | WO9729694 | 8/1997 |
| WO | WO9912482 | 3/1999 |
| WO | WO9940850 | 8/1999 |
| WO | WO9947050 | 9/1999 |
| WO | WO0112084 | 2/2001 |
| WO | WO02102226 | 12/2002 |
| WO | WO03028541 | 10/2003 |
| WO | WO2004012606 | 2/2004 |
| WO | WO2004021894 | 3/2004 |
| WO | WO2004028402 | 4/2004 |
| WO | WO2004086986 | 10/2004 |
| WO | WO2006034209 | 3/2006 |
| WO | WO2007089603 | 8/2007 |
| WO | WO2008147555 | 12/2008 |
| WO | WO2010062380 | 6/2010 |

OTHER PUBLICATIONS

International Preliminary Report on Patentability dated Jan. 27, 2006 and Written Opinion dated Nov. 1, 2007 for PCT/US07/02204.
International Search Report and Written Opinion dated Mar. 3, 2003 for PCT/US02/12560.
International Preliminary Examination Report dated Mar. 12, 2004 for PCT/US02/12560.
International Search Report and Written Opinion dated Jul. 5, 2010 for PCT/US09/06212.
Supplemental European Search Report dated Mar. 15, 2007 for EP140654.5.
European Search Report dated Feb. 8, 2011 for EP10009831.8.
European Search Report dated Feb. 9, 2011 for EP10009832.6.
Office Action dated Jul. 1, 2014 from Corresponding Japanese Application No. 2013-138559.
European Search Report dated Jun. 5, 2015 from corresponding European Application No. 12822057.1.
European Search Report dated Aug. 14, 2015 from corresponding European Application No. 11830008.

(56) References Cited

OTHER PUBLICATIONS

International Search Report issued in related PCT application No. PCT/US07/002204 dated Nov. 1, 2007.
Written Opinion issued in related PCT application No. PCT/US07/002204 dated Nov. 1, 2007.
Search Report dated May 20, 2010 from SG Application No. 200805426-4.
Extended Search Report dated Feb. 17, 2011 from corresponding European Application No. 05797831.4.
Extended Search Report dated Feb. 21, 2011 from corresponding European Application No. 10009831.8.
Extended Search Report dated Feb. 21, 2011 from corresponding European Application No. 10009832.6.
European Search Report dated Mar. 11, 2011 from corresponding European Application No. 07762862.6.
Japanese Office Action dated Oct. 18, 2011 from Corresponding Japanese Application No. 2008-552444.
International Preliminary Report on Patentability dated Feb. 11, 2014 from Corresponding PCT Application No. PCT/US12/049979.
International Search Report and Written Opinion of International Searching Authority (ISA) dated Apr. 24, 2012 relating to PCT/US11/054334.
Examination Report issued by Hungarian IP Office on behalf of Singapore IP Office issued Feb. 8, 2012 in connection with Singapore Application No. 200907505-2.
Supplementary European Search Report dated Mar. 23, 2007 in connection with EP Application No. 02725747.6.
Supplementary European Search Report dated Oct. 6, 2009 in connection with EP Application No. 02725747.6.
Office Action with English translation in connection with Japanese Patent Application No. JP2007-532595 issued Jan. 4, 2011.
Extended Search Report in connection with EP05797831.4 issued Feb. 25, 2011.
Written Opinion issued Jan. 11, 2011 in connection with Singapore Patent Application No. 200907505-2.
International Search Report and Written Opinion dated Jan. 5, 2009 in connection with PCT/US08/006674.
International Preliminary Report on Patentability dated Nov. 24, 2009 in connection with PCT/US08/006674.
International Search Report issued in related PCT application No. PCT/US09/006212 dated Jul. 5, 2010.
International Search Report issued in related PCT application No. PCT/US05/33507 dated Jun. 13, 2008.
Extended Search Report dated Nov. 29, 2012 from corresponding European Application No. 09829467.1.
Ethicon Exhibit 1001 in IPR Case No. 2016-00071; U.S. Pat. No. 6,923,819, issued Aug. 2, 2005, 32 pages.
Ethicon Exhibit 1002 in IPR Case No. 2016-00071; Prosecution History of U.S. Appl. No. 10/127,254, filed Apr. 22, 2002, 359 pages.
Ethicon Exhibit 1003 in IPR Case No. 2016-00071; Expert Declaration of Kevin L. Houser, M.S., dated Oct. 22, 2015, 105 pages.
Ethicon Exhibit 1004 in IPR Case No. 2016-00071; U.S. Pat. No. 5,437,681, issued Aug. 1, 1995, 15 pages.
Ethicon Exhibit 1005 in IPR Case No. 2016-00071; U.S. Pat. No. 5,306,281, issued Apr. 26, 1994, 12 pages.
Ethicon Exhibit 1006 in IPR Case No. 2016-00071; U.S. Pat. No. 4,557,265, issued Dec. 10, 1985, 4 pages.
Ethicon Exhibit 1007 in IPR Case No. 2016-00071; U.S. Pat. No. 6,053,908, issued Apr. 25, 2000, 9 pages.
Ethicon Exhibit 1008 in IPR Case No. 2016-00071; U.S. Pat. No. 5,911,727, issued Jun. 15, 1999, 12 pages.
Ethicon Exhibit 1009 in IPR Case No. 2016-00071; N. Chironis, Mechanisms, Linkages, and Mechanical Control, 5th ed. 1965, 8 pages.
Ethicon Exhibit 1010 in IPR Case No. 2016-00071; "Webster's New Universal Unabridged Dictionary," 2nd Edition 1983, 4 pages.
Exhibit 2001 in IPR Case No. 2016-00071; U.S. Pat. No. 5,709,693, issued Jan. 20, 1998, 7 pages.
Petition for Inter Partes Review of U.S. Pat. No. 6,923,819, dated Oct. 22, 2015, 64 pages.
Patent Owner's Preliminary Response in IPR Case No. 2016-00071, dated Jan. 29, 2016, 49 pages.
Decision on Petition for Inter Patrtes eview of U.S. Pat. No. 6,923,819 in IPR Case No. 2016-00071, dated Apr. 28, 2016, 17 pages.
Non-Final Office Action in U.S. Appl. No. 15/260,094, dated Jan. 17, 2017, 14 pages.
Preliminary Amendment filed in U.S. Appl. No. 15/260,094, dated Nov. 18, 2016, 7 pages.

DEVICES AND METHODS FOR SURGICAL SUTURING

CROSS-REFERENCE TO RELATED APPLICATIONS

This application is a continuation of and claims the benefit of priority to U.S. patent application Ser. No. 15/260,094, filed Sep. 8, 2016, which issued as U.S. Pat. No. 9,649,107, which is a continuation of and claims the benefit of priority to U.S. patent application Ser. No. 13/197,870, filed Aug. 4, 2011, which issued as U.S. Pat. No. 9,445,807, which in turn is a continuation of and claims the benefit of priority to U.S. patent application Ser. No. 11/387,127, filed Mar. 22, 2006, which is issued as U.S. Pat. No. 8,066,737, which is in turn a divisional of and claims the benefit of priority of application Ser. No. 11/121,810, filed on May 4, 2005, which is abandoned, and which is in turn a divisional of and claims the benefit of priority of application Ser. No. 10/127,254, filed on Apr. 22, 2002, now U.S. Pat. No. 6,923,819, which in turn claims the benefit of priority to U.S. Provisional Application Ser. No. 60/298,281, filed on Jun. 14, 2001. Each of the aforementioned patent applications is incorporated by reference herein in its entirety for any purpose whatsoever.

FIELD OF THE DISCLOSURE

The present disclosure relates to a surgical device for suturing tissue. More particularly, the present disclosure relates to a suturing device that enables the manipulation and control of the suturing needle and suturing material during operation, and methods for using such a device for suturing tissue.

BACKGROUND OF THE DISCLOSURE

Sutures are used in a variety of surgical applications including closing ruptured or incised tissue, soft tissue attachment, anastomosis, attachment of grafts, etc. Conventionally, suturing of ruptured or incised tissues, for example, is accomplished by the surgeon passing the sharpened tip of a curved suturing needle with a suture attached to the opposite blunt end of the needle through the incised tissue segments to be sutured such that the needle tip penetrates the tissue segments causing the needle to span the incision. The needle is then pulled through the tissue segments manually causing the attached suture to follow the curved path of the needle. Usually a knot is tied at the trailing end of the suture to anchor the first stitch. This action is performed repetitively with application of tension to the needle to pull the entire suture through the tissue segments through subsequent stitches until the entire incised segments are sutured together with a plurality of stitches.

For example, conventional, open abdominal surgery, including OB-Gyn procedures such as Cesarean delivery, creates a substantial incision (typically eight or more inches in length) in the fascia. In major orthopedic surgery, such as total hip replacement, even longer incisions in two layers of fascia must be closed. The closure of fascia must be done carefully at the conclusion of the surgical procedure, prior to skin closure. Closing fascia by hand suturing is a routine, repetitive, and time-consuming procedure. Typical abdominal incisions may take as long as twenty minutes, while in the case of hip replacement surgery, fascia closure can take even longer. Alternative mechanical suturing devices, as well as staplers, bone anchors, and suture-based arterial closure devices have been used as alternatives to hand suturing in other applications, since manual suturing is a tedious and the speed of the procedure is mostly dependent on skill of the surgeon. Moreover, manual suturing involves the handling and manipulation of a sharp suturing needle with an instrument such as a needle forceps, which can result in slipping and inadvertent, accidental needle pricks through a surgeon's or nurse's gloves, posing a potential risk of infection for the surgeon, nurse, staff, and patient. Furthermore, the direct handling of the needle can cause the needle to become contaminated with pathogenic bacteria that can cause onset of infection at the site of the sutures. There is also a risk of the needle penetrating the bowel and causing a serious, and often fatal infection.

Suturing devices described in the art designed to overcome these limitations are, however, either unduly complex design and economically non-viable or relatively difficult to use and unsuited for precise manipulation for suturing areas that are not easily accessible. For example, the device disclosed in U.S. Pat. No. 4,557,265 has to be held sideways in relation to the direction of the incision being closed. Another limitation of prior art suturing devices is their inability to provide positive control over the needle and suture during the suturing process. This can result in non-uniform sutures with either overly loose or overly tight stitches, which can cause excessive bleeding and risk tearing the repaired tissue in the patient.

A suturing device that maintains a positive control over the suturing needle and is capable of providing uniform stitches is disclosed in U.S. Pat. Nos. 5,437,681 and 5,540,705. The disclosed device requires a "scissors-like" grip and is operated by the surgeon's thumb that provides articulation of the drive mechanism that causes rotation of a linear drive shaft encased in a barrel, which in turn causes a suturing needle encased in a disposable cartridge mounted at the distal end of the barrel to rotate in an advancing motion through the tissue. The device is, however, limited in its efficient operability in the following ways: (1) the rotational direction of the needle and the drive shaft is in a direction that is perpendicular to the device actuating handles, thereby rendering the device relatively difficult to manipulate and control, (2) does not allow the user to view the needle and its progress through the tissue during the suturing operation, since the barrel containing the drive shaft leading to the needle cartridge does not have an open construction to permit such observation, because the action of the needle is blocked from user's view by the nature of the instrument design, thereby making it difficult for the user to position the advancing needle with high accuracy along the junction of the incised tissue segments and (3) the rate of needle advancement and, therefore, the size and uniformity of the stitches is essentially controlled by the user by the extent to which the articulation mechanism is depressed, thereby rendering the process of obtaining uniform needle rotation, tissue penetration and suture advancement difficult and entirely dependent on the skill of the user.

SUMMARY OF THE DISCLOSURE

The present disclosure provides a suturing device that closely emulates or replicates the manual suturing actions carried out by a surgeon. The suturing device of the present disclosure provides greater ease of use and allows better visualization for the user during its operation than present mechanical suturing methods, while maintaining control over needle movement, advancement and suturing thread management during all phases of the suturing process, thereby preventing entanglement of the suturing thread material during needle movement.

A benefit provided the suturing device of the present disclosure is that it enables maneuvering a suturing material through a tissue incision in a manner substantially similar to the way a surgeon would do so by hand. In particular, the suturing device first pushes a suturing needle from the tail of the needle and drives the point of the needle through the tissue. The device then picks up the point of the needle after it has been driven through the tissue, and pulls the remainder of the suturing needle and the suture attached to the suturing needle through the tissue. The suturing needle thus consistently follows the arc of its own curve, which is the preferred method of suturing, in the most non-traumatic way of passing a needle through tissue. A benefit provided by the suturing device of the present disclosure is the ability of the suturing needle to pull the suturing thread entirely through the tissue segments being closed, following each stitch. The present disclosure also relates to a suturing device comprising a suturing needle that is protected by a housing cartridge, whereby the suturing needle is not exposed to or handled directly by the user, thereby precluding inadvertent needle sticks. The configuration of the suturing device of the present disclosure also protects against inadvertent penetration of a bowel by the needle, since the cartridge acts as a shield between the bowel and the needle.

The suturing needle of the present disclosure is configured to fit into a cartridge, which in turn, is removably attached to the distal end of the suturing device. The present disclosure further provides an actuating means and a shaft and drive assembly that provides a torqueing force to the suturing needle to cause the needle to advance through tissue during a suturing process without inadvertent retraction.

The suturing device of the present disclosure offers several advantages over conventional methods used by surgeons for suturing tissue in that it provides a hand-held suturing instrument of relatively simple mechanical construction and which requires no external motive source. Embodiments of the present disclosure provides relative ease of operation for the surgeon with only one hand, thereby enabling the surgeon to move obstructing tissue, debris and biological fluids from the suturing site with a free hand, while eliminating the need for needle holders, pick-up forceps, and other tools normally required for suturing by hand. Furthermore, the suturing devices of the present disclosure can be configured as to length, tip, needle, suture, and needle cartridge size for use in conventional open surgery as well as in minimally invasive surgery (MIS) and in "less-invasive" surgery, such as through natural orifices or through small incisions. Additionally, the suturing head can be oriented in any preferred direction and either fixed in a particular orientation, or rendered movable in a variety of orientations by an articulation means.

These and other advantages of the present disclosure will be apparent through the embodiments described hereinafter. Embodiments of the present disclosure accordingly include the features of construction, combination of elements and arrangement of parts that will be exemplified in the following detailed description.

The surgical suturing devices of the present disclosure is configured to provide a "pistol like" grip for the user that includes a barrel assembly and a handgrip that extends from the proximal end of the barrel. The barrel assembly has either a linear or non-linear configuration, including but not limited to, straight, curved and angled configurations. The barrel assembly comprises a plurality of hollow segments capable of being coupled together by one or more universal joints that do not require a permanent connection between the segments, enabling segments to be pulled apart individually and separated. A cartridge holder is removably attached to the distal end of the barrel assembly by a plurality of support arms to which is releasably mounted a disposable cartridge that is capable of accommodating a suturing needle and a suturing thread material.

The disposable cartridge has a generally cylindrical housing with an aperture in the sidewall of the housing at the distal or working end thereof. An arcuate suturing needle having a sharp, pointed tip at one end of the needle is slidably mounted in a circular track at the distal end of the housing and opposite to the location of the aperture. The needle is connected to a terminal end of a suturing material or thread with a suturing thread source, such as for example, a spool assembly that is contained either entirely within, or remains external the cartridge. The radius of the arc defining the arcuate suturing needle is approximately equal to the circumference to the cartridge housing at the aperture therein. The needle normally resides in a "home" position in its track such that the gap in the arcuate suturing needle is in alignment with the aperture in the cartridge housing. The sharp, pointed end of the needle is situated on one side and entirely within the confines of the housing aperture; the pointed end is, therefore, always shielded by the cartridge housing. The blunt end of the suturing needle that is attached to the suturing thread is located at the opposite side of the aperture. The sharp, pointed end of the needle is, therefore, wholly contained within the cartridge and does not protrude and be exposed to the user.

In accordance with the present disclosure, the needle may be releasably engaged by a driving means that is rotatably mounted within the barrel assembly so that the needle can be rotated from its home position by about 360° about the central vertical axis of the cartridge. Such a rotatory action of the needle causes its sharp tip to advance across the cartridge housing so as to span the aperture. Thus, when the device is positioned such that the incised tissue segments to be sutured are situated at the housing aperture, the needle penetrates the tissue segments and spans the incision between them. A continued rotatory movement of the needle causes it to return it to its original "home" position, and thereby causes the suturing thread attached to the needle to be pulled into and through the tissue in an inward direction on one side of the tissue incision, and upwards and out through the tissue on the opposite side of the incision. Thus, the suture follows the curved path of the needle to bind the tissues together with a stitch of thread across the incision in a manner identical to that of a surgeon suturing manually, wherein the needle is "pushed" from the tail and then "pulled" from the point by the drive mechanism. Preferably, an anchoring means is provided at the trailing terminal end of the suturing material to prevent the material from being pulled completely through and out of the tissue segments. For example, the anchoring means can be a pre-tied or a welded loop, a knot wherein the suture is simply tied, or a double-stranded, looped suture is that attached to the suturing needle.

The rotatory movement of the needle within the needle cartridge is accomplished by a needle driver that may be operated by the user by holding the suturing device with one hand in a pistol-like grip around the handle, and using at least one finger of that hand to activate a triggering lever. The suturing device includes a finger operated trigger lever located proximally to the handle, which when actuated, operates a drive shaft encased within the universal joint barrel assembly through a drive mechanism so as to cause the drive shaft to undergo a rotatory motion, thereby causing the suturing needle to advance in a circular motion. Thus, by placement of the device with the needle cartridge aperture spanning the incised tissue segments and actuating the trigger lever, the suturing device enables the user to lay down a running stitch or interrupted stitch to close the tissue incision in a time efficient manner.

The needle cartridge of the present disclosure is disposably mounted on a cartridge holder assembly that is removably attached to the distal end of the universal joint barrel assembly. The cartridge holder assembly is supported by a plurality of support arms that extend from the distal end of the universal joint barrel assembly. The minimalized structural design of the support arms enables the user to have a clear, unobstructed view of the suturing needle as it advances through the tissue segments during the course of a suturing operation, thereby enabling precise placement of the suturing device to provide uniform sutures and precluding the risk of tearing tissue by its placement too close to the edge of the incision. The suturing devices of the disclosure is then advanced a short distance along the incision and the aforementioned operation is repeated to produce another stitch comprising the suturing material. The suturing devices of the disclosure can either pull the entire suture material through the tissues automatically under controlled tension thereby replicating the actions of a surgeon suturing manually so as to tighten the formed stitches without tearing tissue. Alternatively, the surgeon simply pulls the thread by hand to tighten the stitch placed over the incised tissue segments by passage of the suturing needle of the suturing devices of the disclosure.

The user may continue to manipulate the suturing device, alternately advancing and actuating rotation of the needle about an axis that is generally parallel to the direction of advancement to create a continuous suture which may extend through the entire length of the incision or a series of interrupted stitches. After each individual stitch is laid down, it is tightened by exerting a pull on the suturing material so that the resultant suture is neat and tensioned uniformly along the length of the incised tissue segments. Therefore, a tight closure of the segments is accomplished and bleeding and tearing of tissue are minimized.

As will be described in greater detail below, the needle driver may be operated by the surgeon holding the instrument with one hand, and using at least one finger of that hand. The suturing device includes a finger-operated lever that is functionally coupled with internal gearing and forms part of a handgrip that is located at one terminal end of the device, that enables the surgeon to efficiently and effectively lay down a running stitch, or a series of interrupted or uninterrupted stitches, to close a tissue incision in a minimum amount of time.

The suturing devices of the present disclosure can additionally include an associated thread management system, which operates in conjunction with the needle driver to control or handle the suturing material or thread during rotation of the suturing needle. For example, the thread management roller pushes the thread away from the track so the suture does not get pinched by the needle as the needle re-enters the track. Thus, there is minimal probability of the thread becoming tangled or hung up during the suturing operation. The thread management system can also include a mechanism whereby the suturing material or thread is controllably "paid out" during the suturing process.

When using the suturing devices of the present disclosure, no ancillary instruments or tools such as needle holders, pick-up forceps or the like are needed to complete the suture.

Also, the suturing device may be configured in different ways with respect to length and angle of the universal joint barrels, the angle between barrel segments and the number and shape of the support arms. The size of the needle, needle cartridge, cartridge aperture and aperture position may also be varied for use in open surgery to perform procedures such as closing of the fascia, skin closure, soft tissue attachment, anastomosis, fixation of mesh, grafts and other artificial materials. The suturing devices of the present disclosure may also be designed with a very small working end or tip at the end of a long rigid shaft or a flexible shaft that can be oriented in any preferred direction so that the instrument may be used for MIS, such as suturing in the course of endoscopic surgery, including laparoscopy, thoracoscopy and arthroscopy, as well as less-invasive surgical procedures.

In addition to offering all of the advantages discussed above, the suturing devices of the present disclosure are relatively simple and cost efficient to manufacture. Therefore, the suturing devices should find widespread suturing applications that include single stitches or continuous stitches, e.g. spiral, mattress, purse string, etc., that are required to close tissue incisions, attach grafts, or the like.

BRIEF DESCRIPTION OF THE DRAWINGS

Embodiments of the present disclosure will be further explained with reference to the attached drawings, wherein like structures are referred to by like numerals throughout the several views. The drawings shown are not necessarily to scale, with emphasis instead generally being placed upon illustrating the principles of the present disclosure.

While the above-identified drawings set forth preferred embodiments of the present disclosure, other embodiments of the present disclosure are also contemplated, as noted in the discussion. This disclosure presents illustrative embodiments of the present disclosure by way of representation and not limitation. Numerous other modifications and embodiments can be devised by those skilled in the art which fall within the scope and sprit of the principles of the present disclosure.

DETAILED DESCRIPTION

Figure 1:
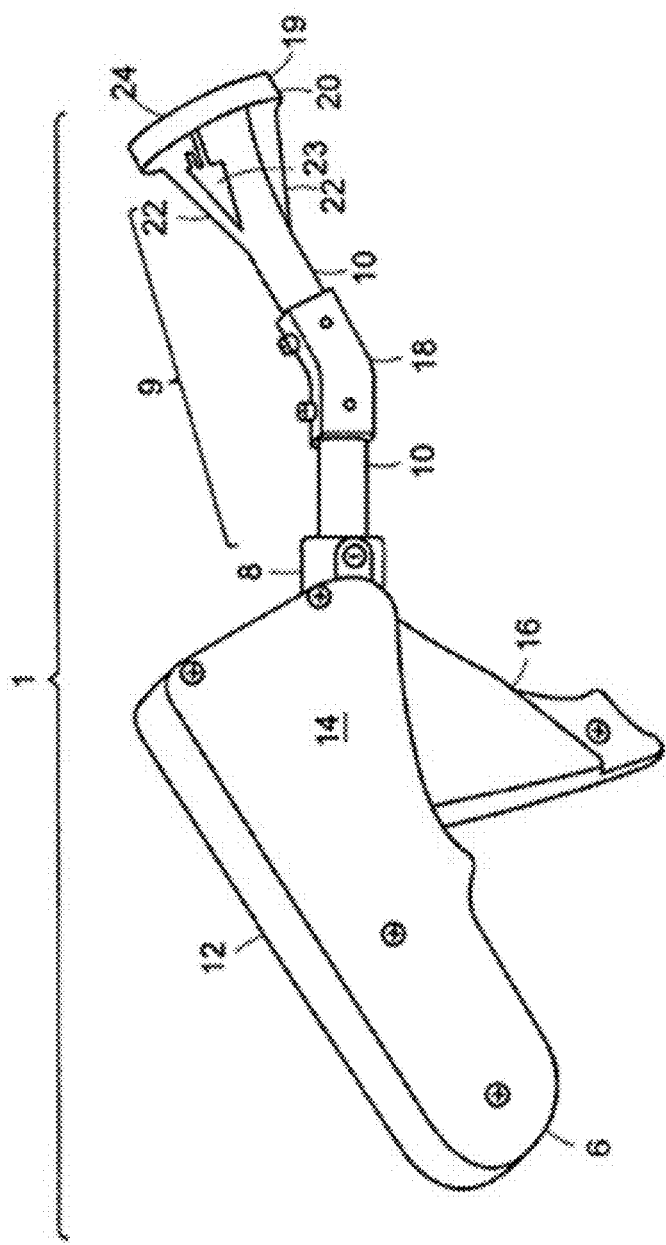
FIG. 1 shows a pictorial view of the suturing device of the present disclosure including the main components of a cartridge, a cartridge holder assembly, drive shaft segments, a universal coupling joint assembly and a sleeve, an actuator handle with an actuating trigger.

The suturing device of the present disclosure is shown generally at 1 in FIG. 1. Referring to FIG. 1, the illustrated suturing device 1 of the present disclosure can be used to produce a continuous or interrupted stitch or suture so as to enable closure of the segments of an incised tissue. The suturing device 1 includes an actuator handle 12 comprising a proximal end 6 and a distal end 8 that allows the device 1 to be held in a pistol grip by the user, and a trigger lever 16. The actuator handle 12 is attached to a pusher 9 at the distal end of handle 12. The pusher 9 comprises a of shaft barrel assembly 10 comprising a plurality of shaft segments capable of housing a drive shaft (not shown) that extend outwardly from a housing 14 at the distal end 8 of the actuator handle 12. The shaft barrel assembly 10 is comprised of at least two segments with symmetric coupling assemblies that are coupled to one another with a universal joint coupler (not shown). The coupled assembly is enclosed within a universal joint sleeve 18 such that the universal joint barrel is configured at an angle of about 30° from horizontal. The shaft segment 10 distal from the actuator handle 12 is attached removably to a support arm assembly 22 that is comprised of a pair of "skeletalized" arms extending along mutually divergent axes so as to provide an opening 23 to view the device working end 19 during its operation. The working end 19 of the suturing device 1 comprises a cartridge holder assembly 20 that is removably attached to the support arm assembly 22, to which the needle cartridge 24 is disposably attached.

FIGS. 2-13 provide detailed views of the various components of one embodiment of the suturing device 1 and the manner in which the components are configured in the final assembled device to enable its operation via a "side-drive" mechanism in the manner described.

Figure 2:
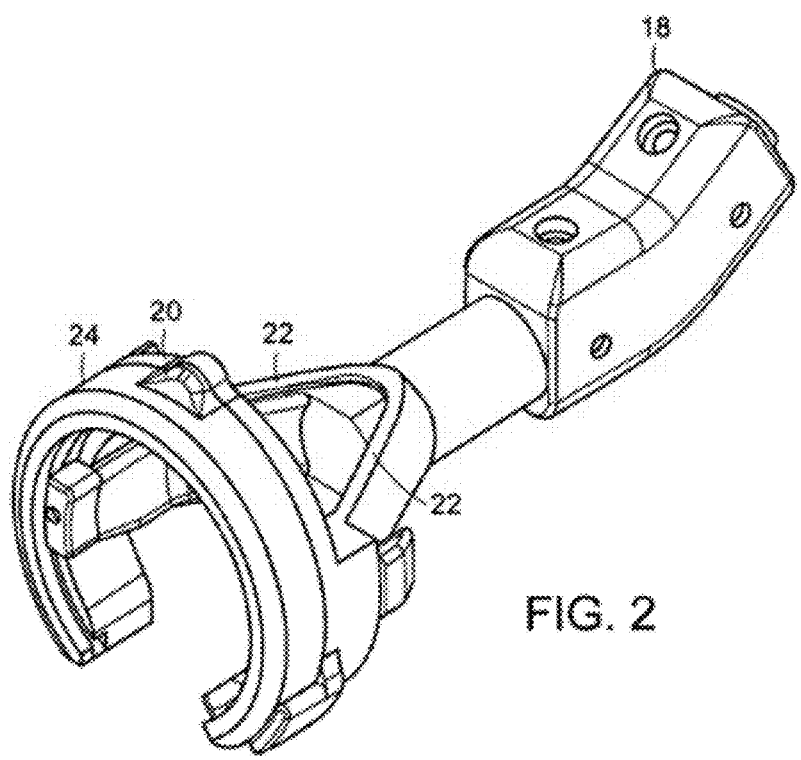
FIG. 2 shows a sectional view of the shaft-universal joint assembly attached to one embodiment of the suturing device functional end comprising the pusher, cartridge assembly and cartridge operable by a side drive mechanism.

FIG. 2 shows the working end 19 of the suturing device 1 including the universal joint coupling sleeve 18, the universal joint segment distal to the actuator handle (not shown) a "pusher" 9 comprising a support arm assembly 22 and a cartridge holder assembly 20 with an attached disposable needle cartridge 24, and a universal joint assembly (hidden) encased in a joint sleeve 18.

Figure 3A:
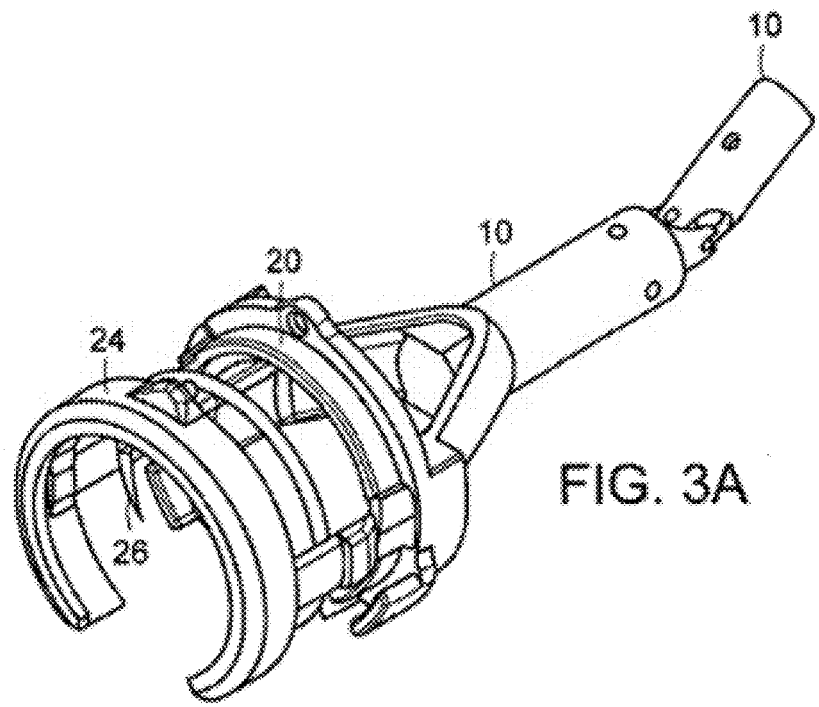
FIG. 3A shows a segmented sectional view of suturing device functional end comprising a universal joint assembly without and with the universal joint sleeve.
Figure 3B:
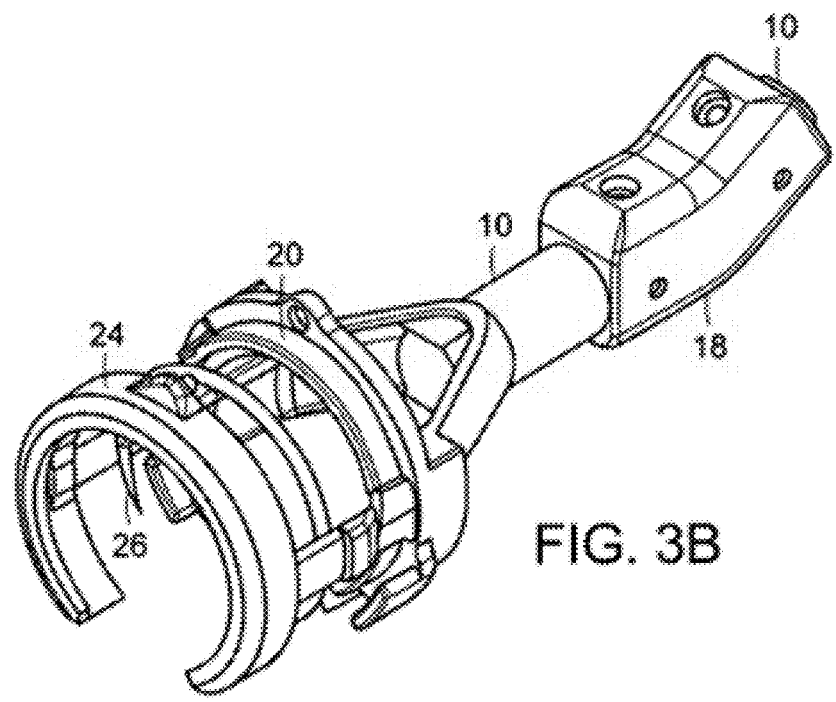
FIG. 3B shows an identical view with the universal joint sleeve.

FIGS. 3A and 3B provide detailed segmental views of the suturing device working-end 19 showing the disposable needle cartridge 24 in a disengaged mode and a curved suturing needle 26 separated from the needle cartridge 24 to illustrate the relative configuration of these segments with respect to the cartridge holder assembly 20, the pusher 9 comprising the support arm assembly 22 and the universal joint segments. FIG. 3A shows the coupled junction mode involving coupling of the shaft segments 10 comprising a universal joint coupler (hidden), while FIG. 3B shows the coupled shaft segments 10 encased in a coupling joint sleeve or "sweep" 18 that aligns the cartridge mount 20 from the stem to the actuator handle at about 30°. The sweep 18 can be either pre-configured to provide a pre-determined fixed angle for the cartridge mount (relative to actuator handle), or can be configured to be adjustable to provide the user with the ability to vary the cartridge mount angle to a setting optimal for a particular procedure.

Figure 4A:
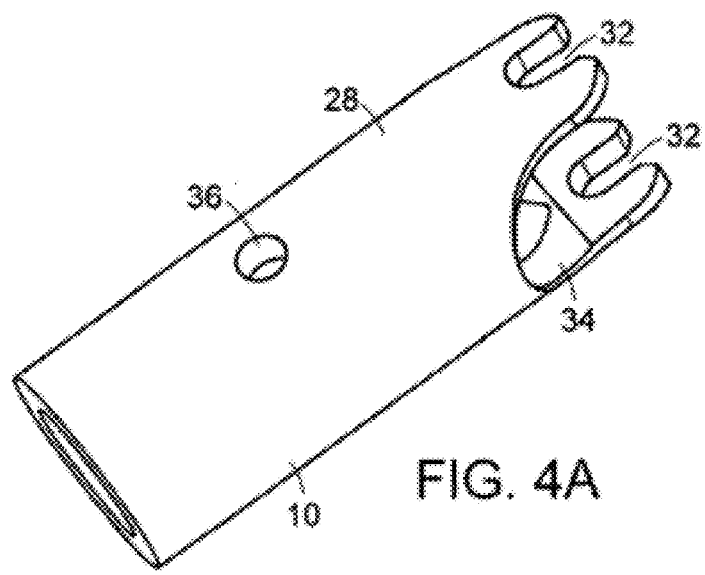
FIGS. 4A, 4B and 4C show enlarged views of a single universal joint, joint coupler and a pair of coupled universal joints respectively.
Figure 4B:
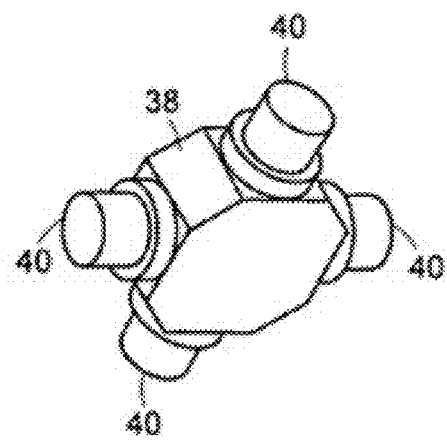
Figure 4C:
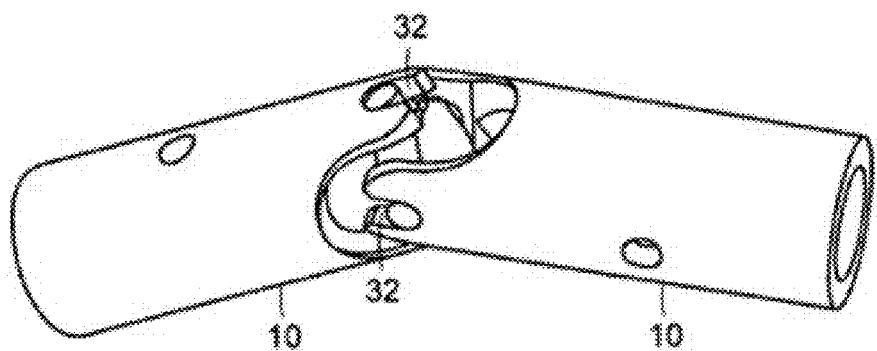

FIGS. 4A-C show expanded views of the hollow universal joint segment and the manner in which two identical segments are coupled. As shown in FIG. 4A, the shaft segment 10 comprises a hollow cylindrical barrel 28 with two open ends, and two pairs of arcuate slots 32 and 34 at one end, wherein one pair of arcuate slots is narrower than the other. Additionally, the joint segment contains a plurality of circular openings 36 located on the cylinder surface to accommodate a corresponding number of restraining pins in the universal joint sleeve ("sweep") 18 that are identical in diameter. Two shaft segments 10 having identical arcuate slot configurations 32 and 34 may be coupled together using a universal joint coupler 38 (FIG. 4B) comprising a plurality of pins 40 such that the coupler engages the pair of narrow slots 32 of the conjoining joint segments 32, thereby providing a junction connecting the two shaft segments 10 that is non-rigid (FIG. 4C). The angle between coupled segments 10 can, therefore, be varied. The coupled segments 10 provide a conduit for passage of a drive shaft (not shown) for activating needle movement.

Figure 5:
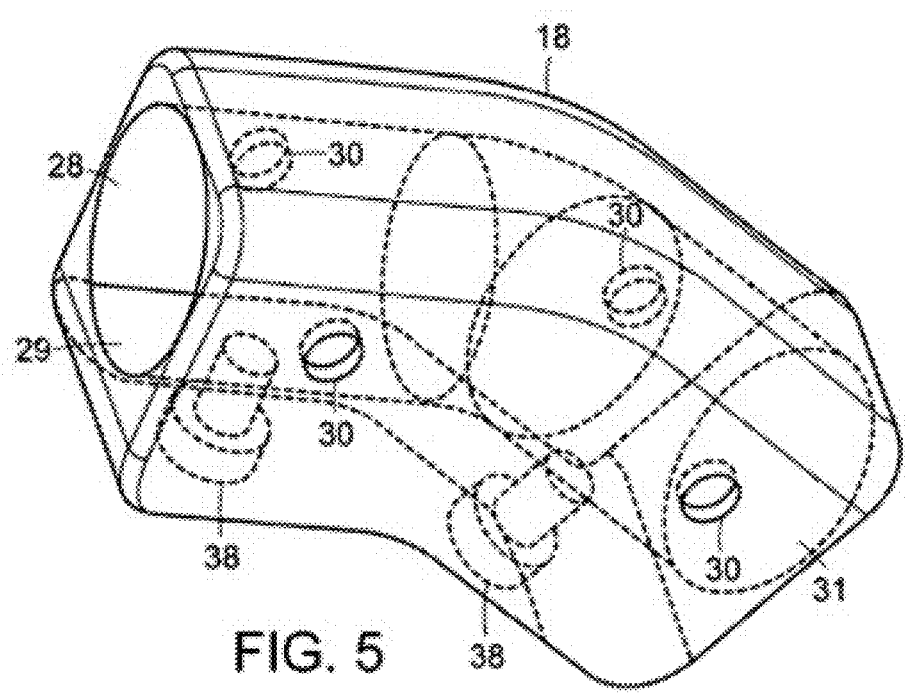
FIG. 5 shows an expanded view of the universal joint sleeve configured at a 30° angle.

FIG. 5 shows a "transparent" view of the universal joint sleeve or "sweep" 18, which comprises of a hollow tubular segment with two open ends 28 whose tubular axis bends over a predetermined angle. The sleeve 18 additionally comprises a plurality of slots 30 positioned along its side wall that are capable of engaging the corresponding circular openings 36 on the shaft segments 10 that are positioned appropriately by means of restraining bolts on pins 38. The sweep 18 therefore, enables the angle of the coupled shaft segments 10 to be "locked" in a preferred angle. The sleeve 18 can be configured to have either a fixed angle, or to have the capability to provide the user the ability to adjust the angle to a preferred setting. In one embodiment, the sweep 18 provides an angle of about 30° from horizontal. The angle for the coupled universal joint segments 10 determined by the sweep in turn, determines the angle of the cartridge holder assembly 20 which is attached to the shaft segment 10 at the distal end 8 of the actuator handle 12 (via the support arm assembly 22). The cartridge holder angle relative to actuator handle 12, in turn, determines the accessibility of the suturing device 1 at the site of the suturing procedure which is critical, depending on whether it is open and planar, or non-planar and narrow.

Figure 6:
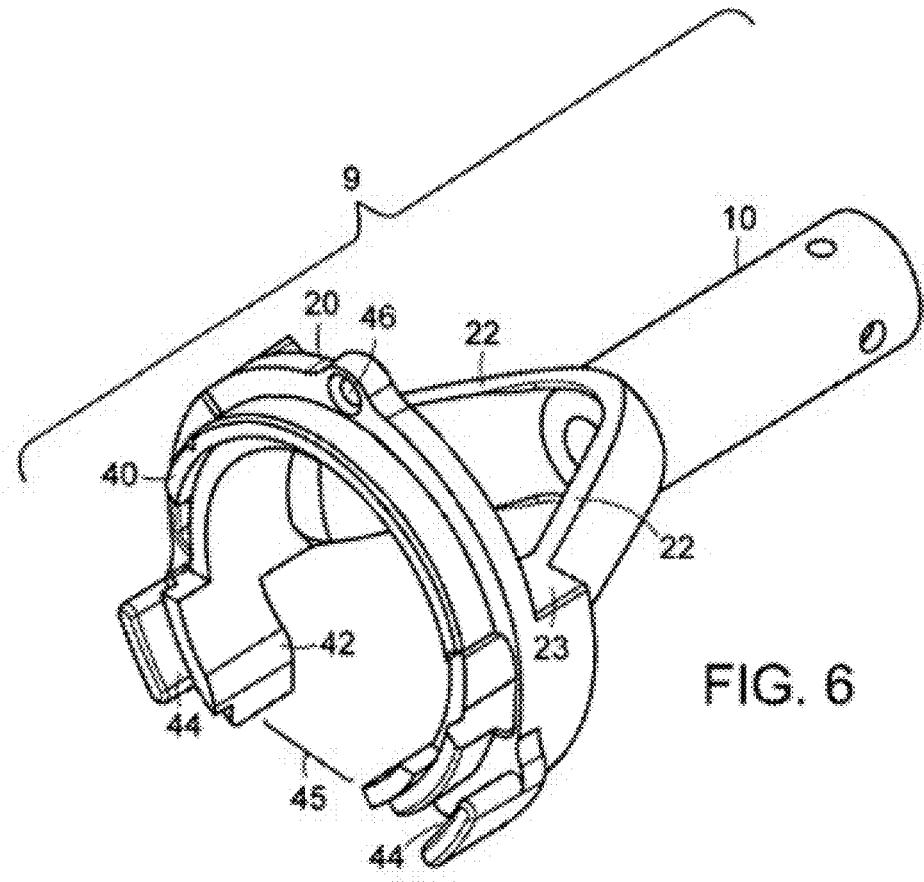
FIG. 6 shows a detailed view of one embodiment of a cartridge mount assembly comprising pair of supporting arms and a shaft segment.
Figure 11A:
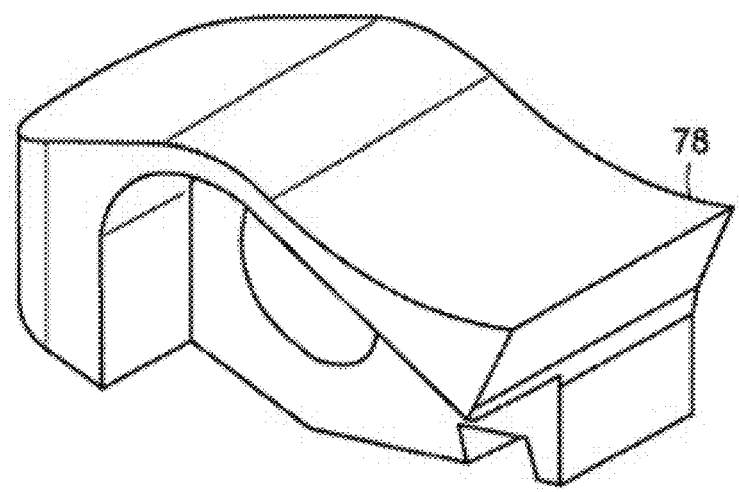
FIG. 11A shows an expanded view of the pawl.
Figure 11B:
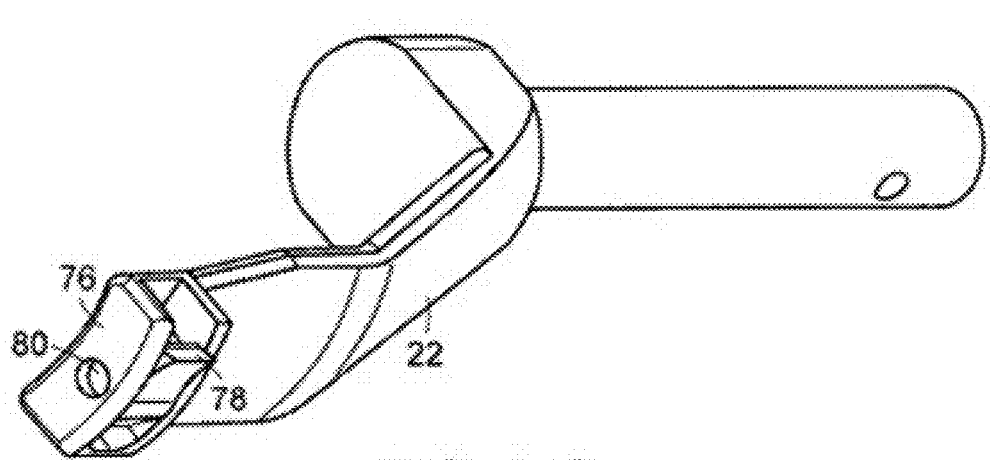
FIG. 11B shows an expanded view of the pusher comprising a cartridge holder support arm with the pawl in place.

FIG. 6 shows a detailed view of the pusher 9 that includes a cartridge holder assembly 20 that is attached to a support arm assembly comprising a pair of "skeletalized" support arms 22 which in turn, is attached to the terminal end of shaft segment 10. The open configuration of the "skeletalized" support arms 22 that are minimal in bulk is an essential feature of suturing device 1 that provides a relatively wide opening 23 that allows the user to directly view the aperture in the needle cartridge and cartridge (not shown) holder assembly 20, the incision in the tissue and needle advancement through the incised tissue segments during operation of suturing device 1. Although the embodiment shown in FIG. 6 has a plurality of support arms 22, other variants include a support arm assembly comprising a single support arm as illustrated in FIG. 11B. The improved viewing ability offered by the shape and configuration of the support arm assembly 22 enables precise device placement over the incision, and uniform advancement of the suturing device after every stitch to provide a uniform and symmetric suture, thereby minimizing the risk of tearing tissue and bleeding due to a stitch being positioned too close to the edge of the incised tissue. The cartridge holder assembly 20 is composed of a sterilizable medical grade material which can either be a metallic material such as stainless steel to enable its reuse subsequent to sterilization following a prior use, or a sterilizable medical grade plastic material, in which case, it may discarded and disposed after a single use. The cartridge holder assembly 20 has a cylindrical configuration with a distal edge 40 and a proximal edge 42 with respect to the device actuator handle (not shown), with an aperture 45 that corresponds in dimension and location to coincide with a substantially similar aperture located in the disposable needle cartridge. The cartridge holder assembly 20 additionally comprises a plurality of slots 44 located along on the distal edge 40 in that are located diametrically opposite to one another, and are capable of engaging the same plurality of retaining clips correspondingly located in the needle cartridge housing (not shown). The cartridge holder assembly 20 further comprises a cylindrical slot 46 located on the distal edge 40 that is capable of engaging a positioning pin of identical diameter correspondingly located on the needle cartridge housing (not shown). The proximal edge 42 of the cartridge holder assembly is attached to the shaft segment 10 distal to the actuator handle 12 via a support assembly comprising at least one "skeletalized" support arm 22.

Figure 7A:
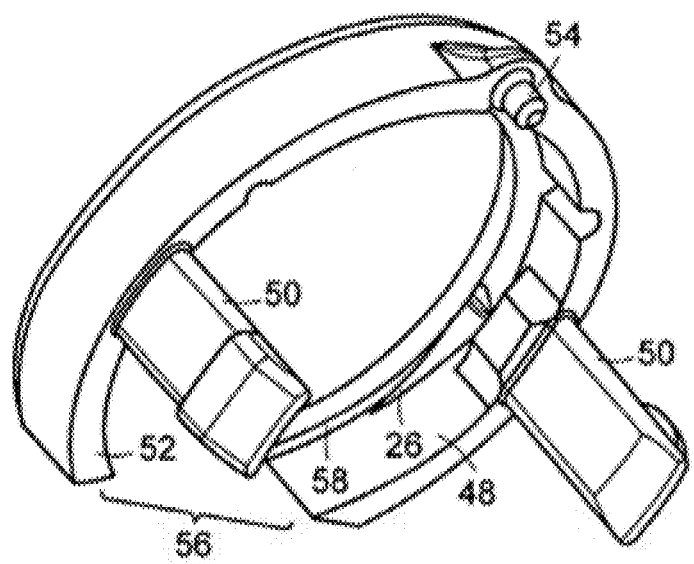
FIGS. 7A and 7B show two different views of one embodiment of the needle cartridge.
Figure 7B:
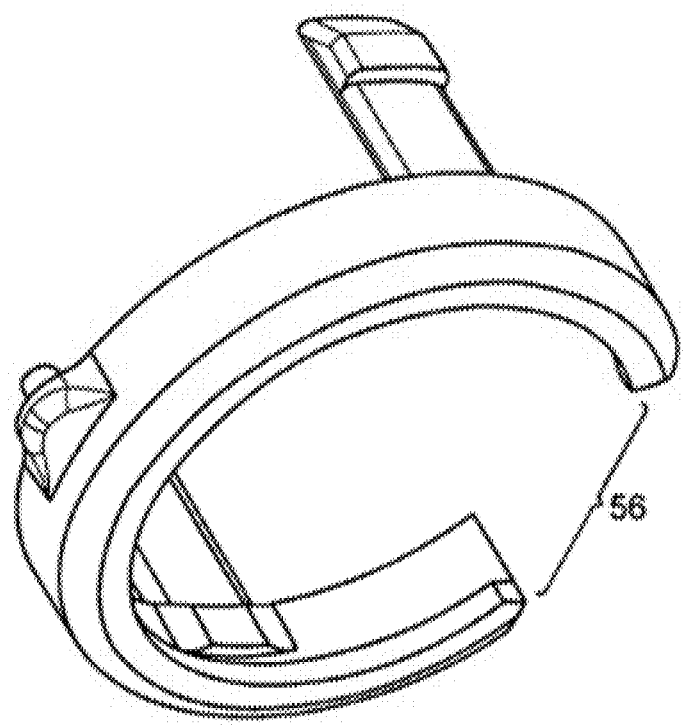

FIGS. 7A and 7B show two different views of an embodiment of a disposable suturing needle cartridge 24 in accordance with the present disclosure, which is preferably offered in a sterilized sealed package. The cartridge 24 comprises a circular housing 48 that may be formed of a suitable rigid medical grade sterilizable metal or plastic material. The housing may be releasably retained by the cartridge holder assembly 20 at the distal end 19 of suturing device 1 (working end) by known means, such as a plurality of clips 50 (shown in FIG. 7A) located along on the edge of an inner lip 52 in diametrically opposite positions that are capable of engaging the same plurality of slots correspondingly located in the cartridge holder assembly 20. The cartridge 24 further comprises a cylindrical positioning pin 54 located on the edge of the inner lip 52 that is capable of engaging a cylindrical slot of identical diameter correspondingly located on the cartridge holder assembly 20. While the retaining clips 50 when engaged enable the cartridge to be retained by the cartridge holder assembly 20, the positioning pin 54 when engaged in the slot causes the aperture in the cartridge 24 to be aligned with the corresponding aperture in the cartridge holder assembly 20. The needle cartridge 24 further comprises an aperture 56 and a circular groove or "track" 58 that is inscribed in the inside surface of the housing 48, which lies in a plane that is perpendicular to the longitudinal axis of both the housing 48 and that of the suturing device 1. As shown in FIG. 7A, the cartridge-housing aperture 56 interrupts the track 58. An arcuate surgical suturing needle 26 composed of medical grade stainless steel or similar material is slidably positioned in the track 58.

Figure 8A:
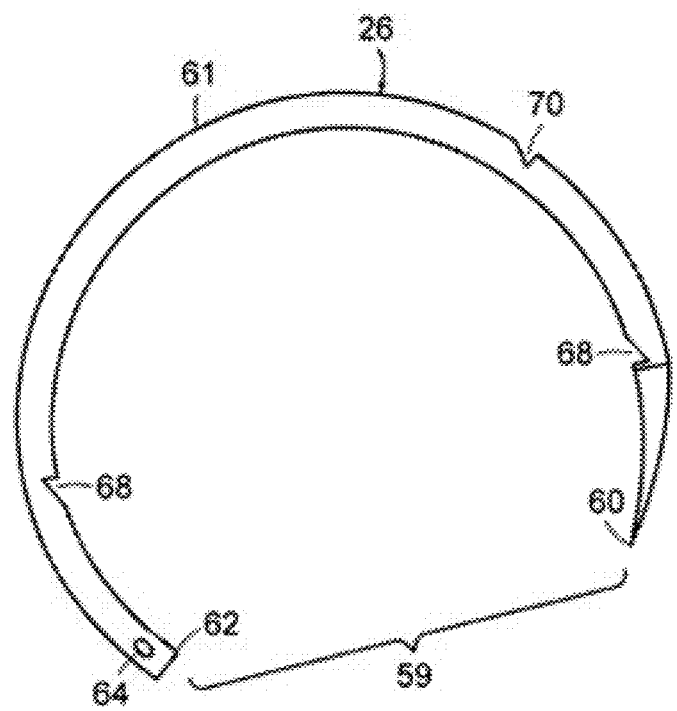
FIGS. 8A and 8B show two embodiments of the curved suturing needle with suture material ports that are operable by a side drive mechanism.
Figure 8B:
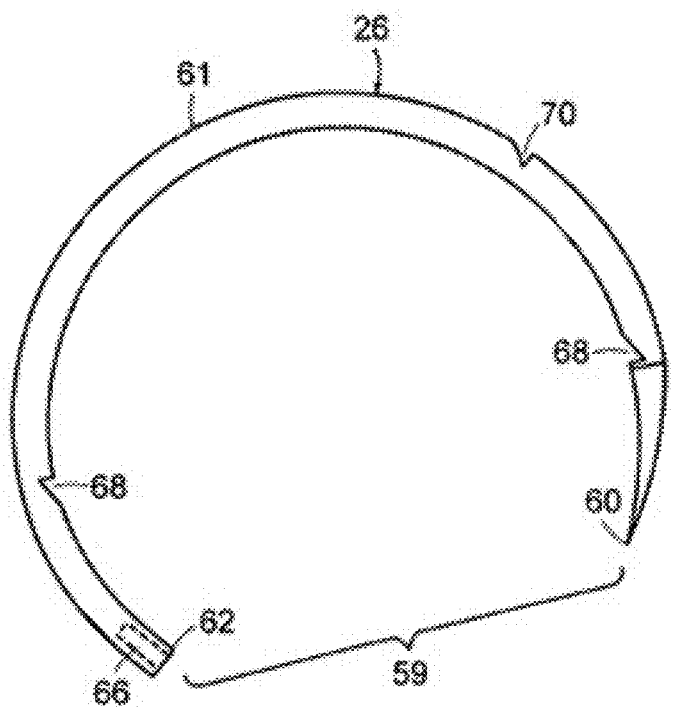

FIGS. 8A and 8B show embodiments of the arcuate suturing needle 26 of the present disclosure. In one embodiment (FIG. 8A), the needle 26 is formed as a circular split ring with a gap 59, a sharp, pointed end 60, and a blunt end 62. The needle 26 further comprises an opening to accommodate the leading end of the suturing material. In one embodiment, the opening is the form of an eye 64 through which the leading end of the suturing material may be passed through for attaching it to the needle 26. In the illustrated needle (FIG. 8A), the eye 64 is located adjacent to the blunt end 62. The eye 64 however, can be positioned anywhere along the arc or the needle 26 between its apex 61 and the blunt end 62. In a preferred embodiment (FIG. 8B), the needle 26 comprises an opening in the form of a cylindrical bore 66 aligned axially with respect to the needle 26, located at the blunt end 62 (FIG. 8B). The leading end of the suturing material is inserted into the bore and restrained by mechanically crimping. To enable the needle 26 to penetrate tissue to the required depth, the needle preferably has an arcuate extent between about 280° and about 330°, and more preferably, greater than about 270°. The needle 26 comprises two symmetric notches 68 along the radially inner edge ("inner notches") that are positioned proximally to the sharp, pointed end 60 and the blunt end 62 of the needle 26. The notches 68 are located directly opposite to each other, each having a perpendicular (about) 90° segment and an angular segment that makes an angle of about 60° with the perpendicular segment. The inner notches 68 are engaged by the drive mechanism in the cartridge holder assembly 20 and enable the needle 26 to undergo a rotatory movement upon actuation of the drive mechanism, thereby causing it to penetrate into and advance through tissue. A similar triangular notch 70 is located on the radially outer edge ("outer notch") of the needle proximally to the inner notch 68 closer to the sharp, pointed end 60. The outer notch 70 engages with an "anti-rotate" pin located in the cartridge holder assembly 20, whereby rotation of the needle 26 in a direction opposite to the advancing direction or "needle backing-up" is prevented. The positive engagement of the needle outer notch 70 during operation of the suturing device 1, and thereby precludes needle 26 from straying out of sequence during the suturing process.

The width of the aperture 56 in the cartridge housing 48 is comparable to and corresponds with the width of the gap in the needle 26 so that when the needle 26 is in the "home" position (as shown in FIG. 7A) it does not project materially into the aperture 56. Such an alignment causes the needle to reside entirely within the cartridge holder 20, thereby preventing inadvertent contact of the sharp pointed end 60 with the user's fingers during handling of the disposable needle cartridge 24 for its placement on the cartridge holder 20 or its disposal after use, and while operating the suturing device 1. Such protection of the needle 26 in the suturing device of the present disclosure prevents accidental "needle-pricks" from occurring, thereby substantially reducing the risk of infection caused by pathogenic bacteria or viruses that may contaminate the needle during or after its use prior to its disposal. The needle 26 may be rotated in its curved track 58 about the longitudinal axis of the suturing device 1 to advance the pointed needle tip 60 so that the needle first spans the aperture and then return to its original or home position. Since the suturing material is attached to the needle 26, it follows the path of the needle 26. The terminal end of the suturing material may contain a knot or button to prevent it from pulling through the sutured tissue during placement of the first stitch. The suturing material or thread may be stored in an enclosed packaging either externally or internally with respect to the needle cartridge housing 48, and be pulled out of that packaging prior to placement of the first stitch in the suturing process. In a preferred embodiment, the cartridge housing 48 comprise the suturing needle 26 attached to the terminal end suturing material or thread, and an appropriate length of suturing material are all packaged in a terminally sterilizable medical packaging material.

Figure 9:
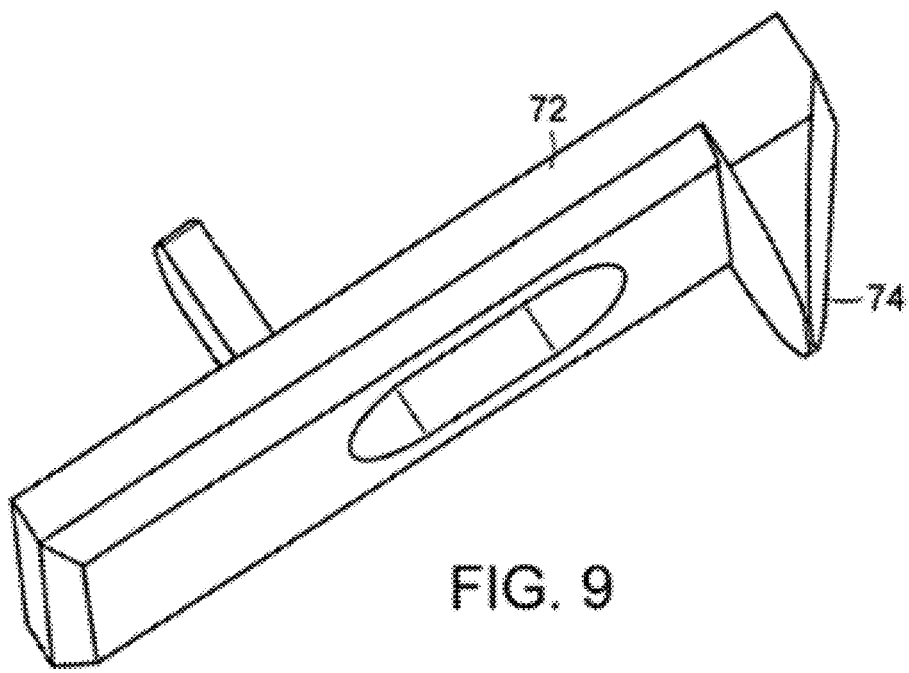
FIG. 9 shows an expanded view of the thread management roller housed in the cartridge.

FIG. 9 shows a thread management roller 72 of the present disclosure which acts to push the thread away from the track so the suture does not get pinched by the needle as the needle re-enters the track. The thread management roller 72 comprises a spring operated stop pin 74 that maintains a positive pressure against the suturing material or thread, thereby preventively retaining the suturing material in the thread retaining slot of the suturing needle, while keeping the thread out of the needle track to preclude the thread from jamming needle movement. The stop pin 74, therefore, prevents jamming of needle movement by an inadvertent entry of the suturing material into the needle slot within the needle cartridge 24 when the material is pulled forward by the advancing movement of the needle 26.

Figure 10:
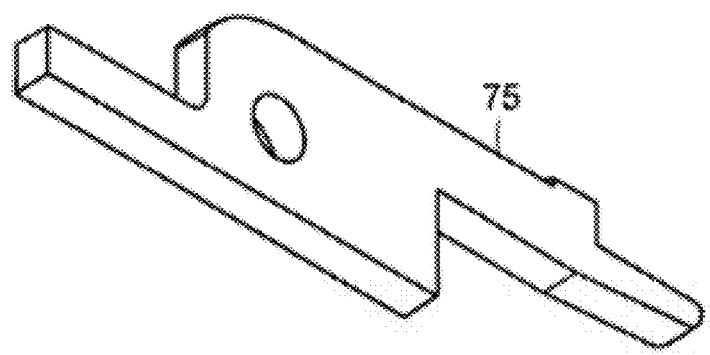
FIG. 10 shows an expanded view of the "anti-rotate" pin housed in the cartridge assembly.

FIG. 10 shows an expanded view of the anti-rotate pin 75 that is capable of engaging the outer notch of the needle 26 to prevent rotation of the needle 26 and prevent "needle backing-up" and thereby precluding the needle 26 from straying out of sequence.

FIG. 11B shows an expanded view of a pusher assembly comprising pusher 76 and a pawl 78 (FIG. 11A) located at its tip, which resides in a corresponding slot in the support arm 22 of the pusher assembly, and is connected the support arm 22 by a pivot pin 80. The needle 26 is driven in a circular path by a rigid arm ("pusher") that extends from a hub located in the center of the suturing device 1. The pawl 78 at the tip of the pusher 76 is capable of interfitting with the wedge shaped notches located along the radially inner edge of the needle. The pusher 76 is activated by the user upon operation of the actuator trigger in the actuator handle 12, and is capable of sweeping back and forth in an arc spanning about 280°. The outer surface of the pusher 76 is shaped to accommodate a C-shaped spring (not shown) that causes the wedge-shaped pawl 78 to push up against the needle 26 and thereby remain in intimate contact. The advancing movement of needle 26 during its operation causes the triangular slots 68 along the radially inner edge of needle 26 align with the wedge-shaped pawl 78 in the pusher 76, thereby causing the pawl 78 to engage the slots 68 due to a positive pressure exerted on the pin by the C-shaped spring, and to "lock" into the slots 68. The rotatory advancing movement of the needle 26 is therefore controlled to occur sequentially through about 280° each time it is actuated.

Figure 12:
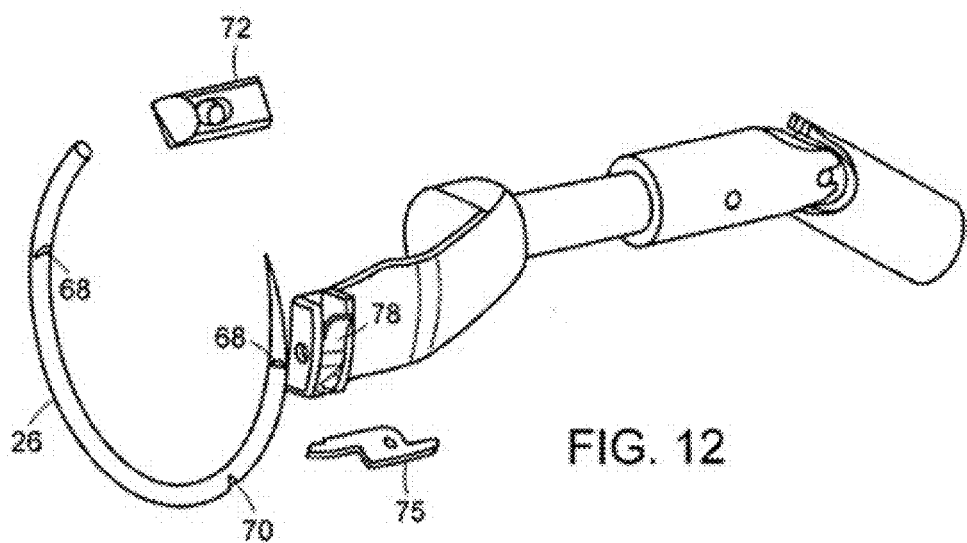
FIG. 12 shows a cut-away segment view showing interaction points of a suturing needle with a cartridge holder and support arm components.

FIG. 12 shows a cut-away segmental view of the needle 26 in the home position inside the cartridge (not shown) with respect to the stem cartridge holder assembly (not shown). The relative locations of the pawl 78 that engages the notches 68 in the radially inner edge of the needle 26, the thread management roller 72 and the anti-rotate pin 75 that engages the notch 70 in the radially outer edge of the needle 26 are shown in FIG. 12.

Figure 13:
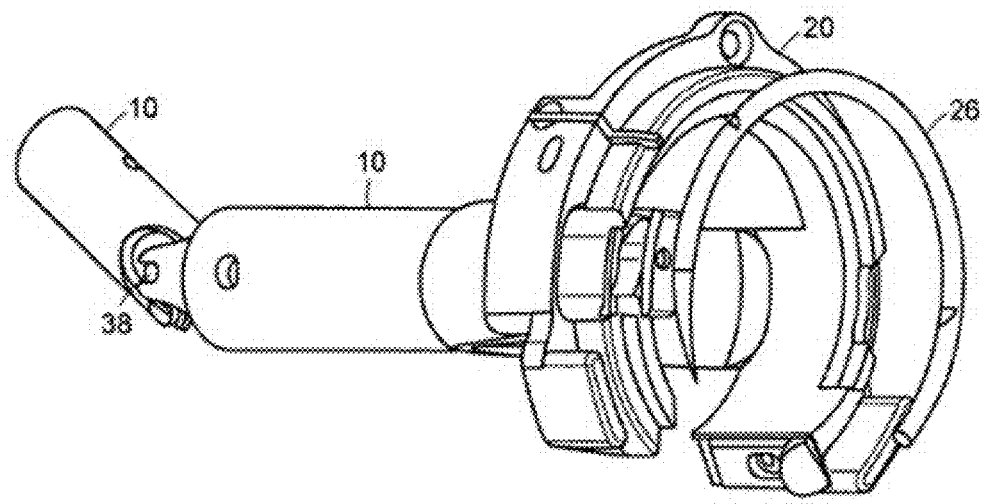
FIG. 13 shows a segmented view of the relative configuration of a suturing needle with respect to the cartridge holder.

FIG. 13 shows a cut-away view of the needle 26 within the cartridge (not shown) in the "home" position, the alignment of the needle aperture with the corresponding aperture in the needle cartridge holder 20, the relative position of the needle 26 and cartridge holder 20 and aperture location with respect to the coupled shaft segments 10 that are coupled by universal joint coupler 38 and maintained at a fixed angle by the restraining coupling sleeve or "sweep" (not shown).

FIGS. 14-20 show detailed component views of a preferred embodiment of the suturing device of the present disclosure and the manner in which the components are configured to enable its operation as described herein.

Figure 14:
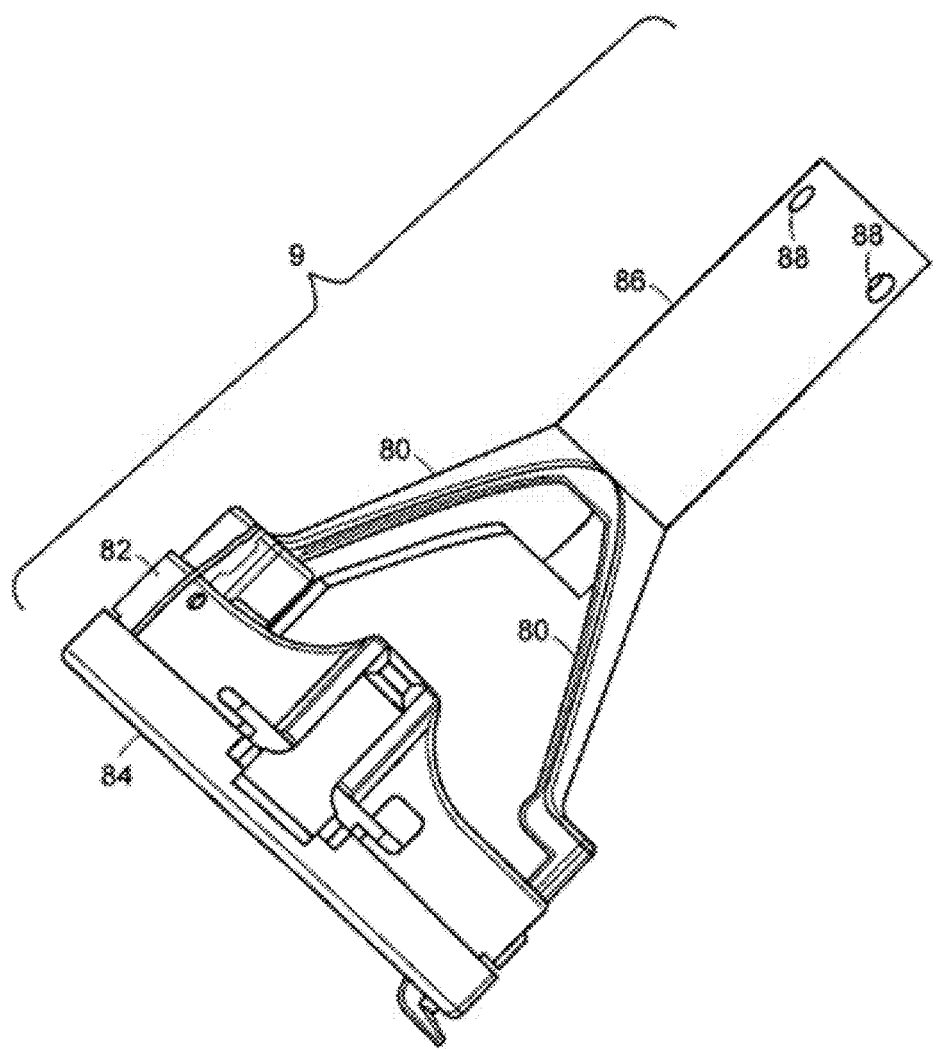
FIG. 14 shows a segmented sectional view of the functional end of a second embodiment of the suturing device operable by a rear drive mechanism comprising a shaft segment, the pusher, cartridge holder and cartridge (shown sectionally in FIGS. 15-19).

FIG. 14 shows the working end of a preferred embodiment of the suturing device of the present disclosure, comprising a "pusher" 9 having a support arm assembly 80 and a cartridge holder assembly 82 with the attached disposable needle cartridge 84. The "pusher" 9 is connected to the drive mechanism via shaft segment 86 that is coupled via a universal joint coupling comprising a universal joint assembly encased in a sleeve (not shown) to a second shaft segment distal to the actuator handle 12. The shaft segment 86 is attached to the universal joint assembly by pins that engage slots 88 with corresponding slots in the coupling assembly.

Figure 15A:
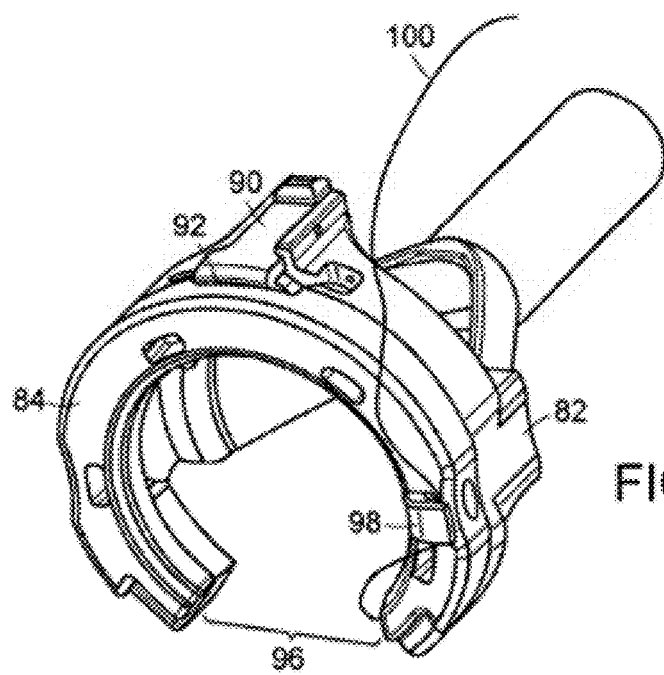
FIG. 15A shows a perspective view of a pusher with a cartridge holder assembly comprising an attached cartridge with a suture threading mechanism for restraining a suture material.

FIG. 15A shows segmental views of the pusher assembly comprising a needle cartridge 84 engaged with cartridge holder assembly 82. The cartridge 84 attaches to cartridge holder assembly 82 via a mounting clip 90 located at the apex of the arc of the cartridge holder assembly 82 that slidably "locks" into position with a complementary slot 92 located correspondingly on the apex of cartridge 84. Both cartridge holder assembly 82 and cartridge 84 comprise an aperture 96 that are of similar dimension, and aligned with one another in the "locked" position. The cartridge 84 further comprises a suturing material management cleat 98 which is capable of restrictibly maintaining suturing material 100 in a manner so as to preclude its entanglement as it travels into cartridge 84 during operation of the suturing device.

Figure 15B:
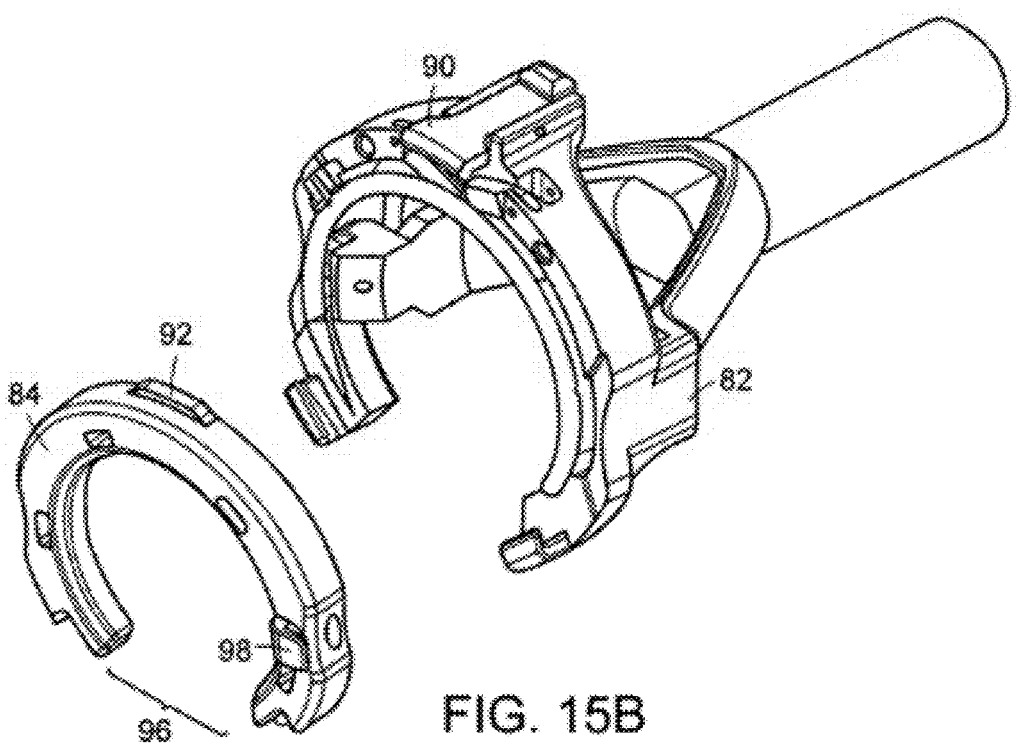
FIG. 15B shows a pusher comprising the cartridge holder assembly and a cut-away section of a cartridge comprising the curved suture needle that is operable by a rear drive mechanism.

FIG. 15B shows a cut-away view of the pusher assembly exposing a suturing needle 102 residing within cartridge 84 (not shown) in the "home" position, wherein the alignment of the needle aperture corresponds with apertures of both needle cartridge holder assembly 82, and the cartridge 84. The needle 102 is placed in the "home" position by engaging cartridge 84 with cartridge holder assembly 82 in a "locked" position, whereupon it is restrained by clip 90 in a manner causing it to be engaged with notches located along the radially rear edge of the needle (not shown) that is proximal to cartridge holder assembly 82 by correspondingly located pins in a drive arm located in the cartridge holder assembly 82 that is part of a "rear-drive" needle rotation drive operating mechanism.

Figure 16:
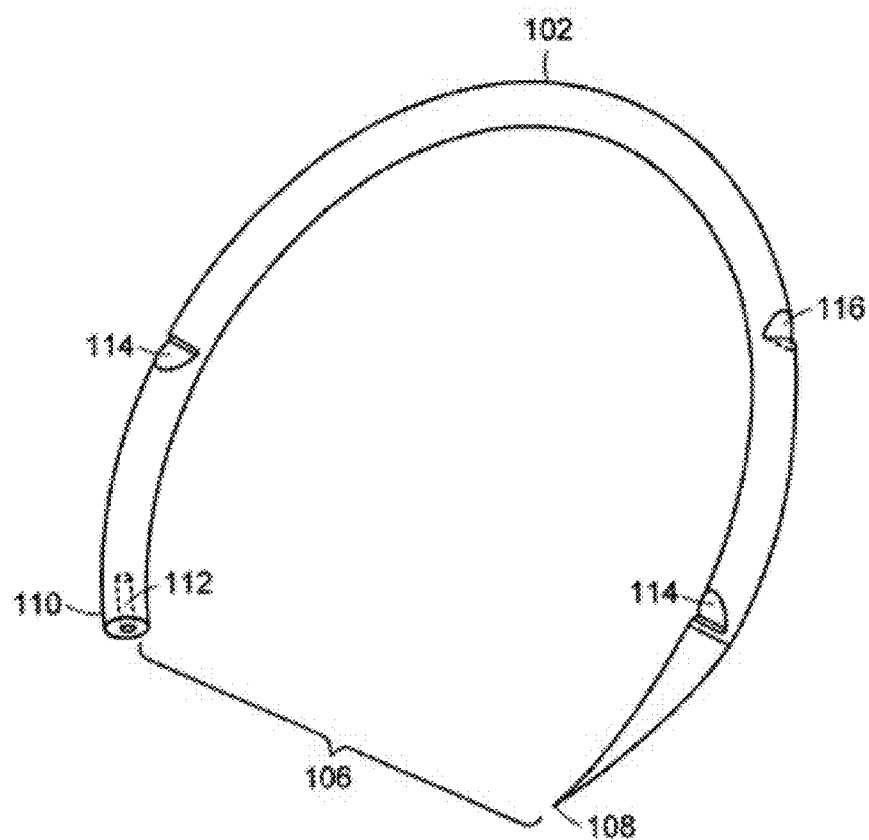
FIG. 16 shows an expanded view of a curved suturing needle with suture material port that is operable by a rear drive mechanism.

FIG. 16 shows a preferred embodiment of the curved suturing needle 102 of the disclosure. The needle 102 is formed as a circular split ring with an aperture (or gap) 106, as sharp, pointed end 108 and the opposite end no. A cylindrical bore 112 aligned axially with respect to the needle, located at the blunted 110. The leading end of the suturing material is inserted into the bore and restrained by mechanically crimping. Alternatively, the opening for accommodating the suture material can be in the form of an "eye" wherein the leading end of the suturing material may be passed through for attaching it to the needle 102. To enable the needle 102 to penetrate tissue to the required depth, the needle 102 preferably has an arcuate extent between about 280° and about 330°, and more preferably, greater than about 270°. Needle 26 comprises two symmetric notches ("rear notches") 114 along the radially rear edge, i.e. the edge proximal to the cartridge holder 82, that are positioned proximally to the sharp pointed end 108 and the opposite blunt end 110 of the needle 102, respectively. The rear notches 114 are located directly opposite to one another, each having a perpendicular (about) 90° segment and an angular segment that makes an angle of about 60° with the perpendicular segment. The rear notches 114 are engaged by the drive mechanism in the cartridge holder assembly and enable the needle to undergo a rotational movement upon actuation of the drive mechanism, thereby causing it to penetrate and advance through tissue. A similar triangular notch 116 is located on the radially outer edge ("outer notch") of the needle proximally to the rear notch 114 that is closer to the sharp, pointed end 108. The outer notch 116 engages with an "anti-rotate" pin located in the cartridge holder assembly, whereby rotation of the needle in a direction opposite to the advancing direction or "needle backing-up" is prevented. The positive engagement of the needle outer notch 116 during operation, therefore, precludes the needle from straying out of sequence during the suturing process.

Figure 17A:
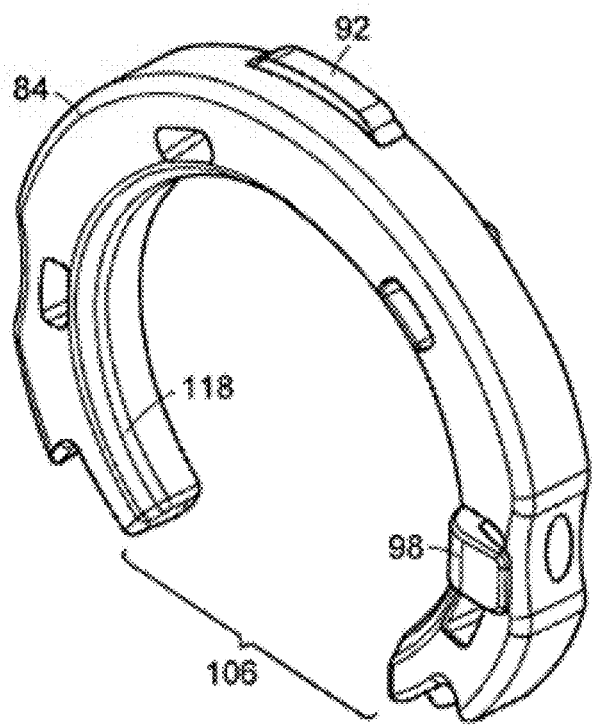
FIGS. 17A and 17B show front and rear views of the cartridge.
Figure 17B:
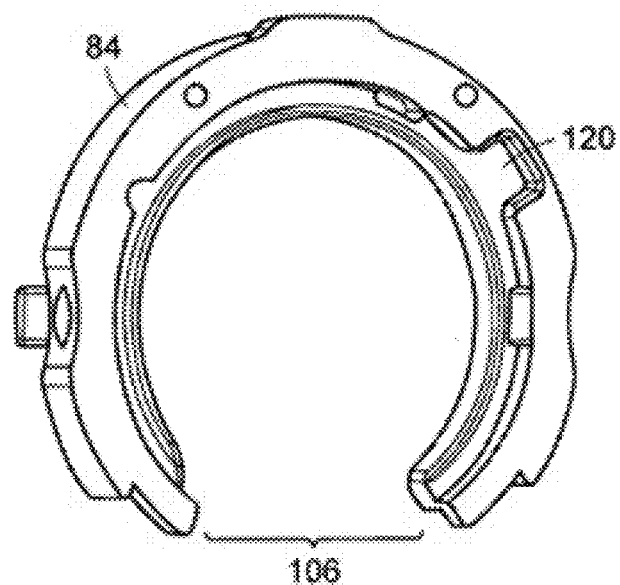

FIGS. 17A and 17B show the outer and inner views, respectively, of the cartridge 84. The outer surface of the cartridge 84 (FIG. 17A) comprises a suturing material management cleat 98 which is capable of restrictibly maintaining the suturing material in a manner to preclude its entanglement. The cartridge 84 further comprises a slot 92 located at the apex of an actuate edge that slidably engages a complementarily located pin on the cartridge holder assembly to "lock" it in position. The inner surface of the cartridge 84 comprises a track 118 that permits the suturing needle (not shown) housed within to travel in a rotational motion from its "home position" so as to span aperture 106 during operation. A slot 120 located radially on the inner surface of cartridge 84 engages with a complementarily located pin on the cartridge holder assembly such that when the pin is engaged slidably in slot 120, the needle is constrained to remain in and move along track 118.

Figure 18:
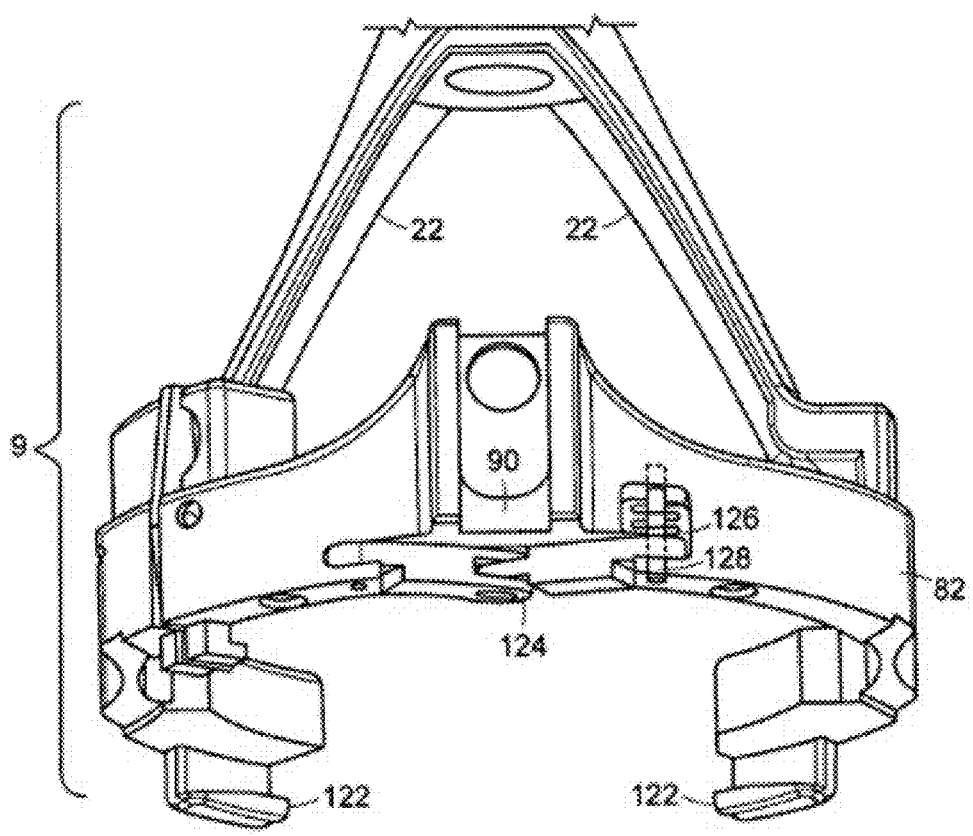
FIG. 18 shows a cut-away sectional top view of a pusher comprising a cartridge holder assembly with a locking gate.

FIG. 18 shows a top sectional view of a preferred embodiment of a "pusher" 9 comprising a cartridge holder assembly 82 and support arms 22. The cartridge holder assembly 82 comprises a plurality of mounting clips 122 that are capable of receiving the cartridge 84, and a mounting clip 90 at the apex of the radial edge and slidably engaging a complementarily located slot in the cartridge that engages cartridge holder assembly 82, thereby causing the drive mechanism in the assembly 82 to engage the suturing needle housed within the cartridge. The cartridge holder assembly 82 further comprises a gate assembly 124 that prevents needle 102 from leaving its track and falling out into the back of the cartridge holder assembly 82. The gate assembly 124 is maintained in a closed "home" position by a torque force exerted by a spring 126 to which it is coupled via a pin 128, thereby restricts lateral movement of needle 102. The gate assembly 124 opens during each actuation of the suturing device to permit a circular movement of the drive mechanism that engages needle 102, and closes to the home position immediately after passage of the drive mechanism to preclude lateral movement and dislocation of needle 102 within cartridge holder assembly 82.

Figure 19A:
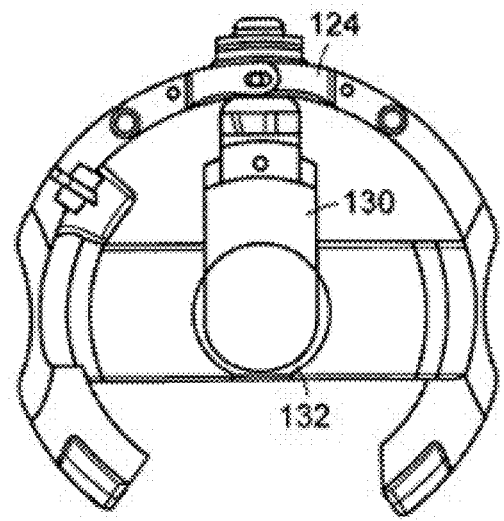
FIGS. 19A, 19B and 19C shows the operation of the pusher arm in a cartridge assembly operating in a rear drive mode. The pusher arm traverses radially by opening the gate (FIG. 19A), which springs to the closed position (FIGS. 19B and 19C) after its passage.
Figure 19B:
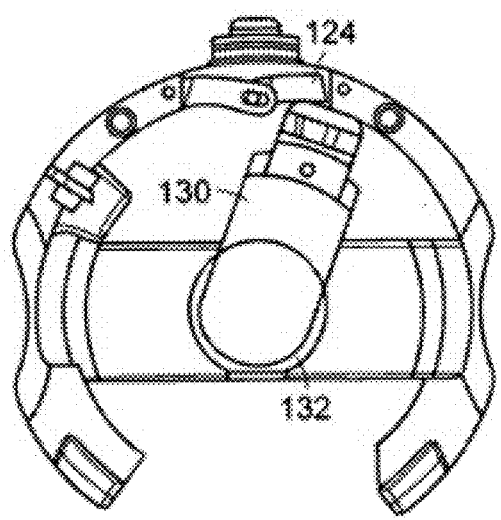
Figure 19C:
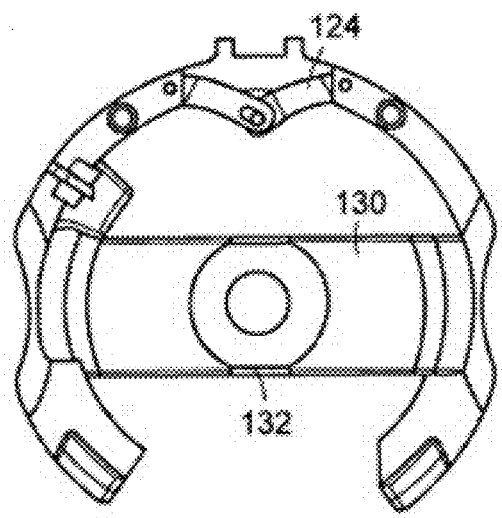

FIGS. 19A, 19B and 19C show serial views of the "rear-drive" needle operating drive mechanism operating within the cartridge holder 82 of the pusher assembly (not shown). The "rear-drive" mechanism comprises a driver arm 130 connected to a drive shaft 132 that is capable of circular motion so as to "sweep" along the circular inner edge of the cartridge holder 82 comprising the gate assembly 124. Actuation of the device causes the drive shaft 132 to rotate in a clockwise direction, thereby causing driver arm 130 to move circularly from its "home" rest position and move up to and the past gate assembly 124, causing it to open in the process (FIGS. 19A and 19B). The driver arm 130 continues to move circularly until it comes to rest once again in the "home" position (FIG. 19C). The gate assembly 124 returns to its closed home position after passage of the driver arm 130, thereby allowing driver arm 130 to "drive" needle 102 in a circular motion, while preventing the needle 102 from becoming dislocated from track 118. Thus, each time suturing device 1 is actuated, driver arm 130 moves past the gate assembly 124, opening the gate assembly 124 in the process. Since the gate assembly 124 moves back into its closed "home" position after passage of the driver arm 130, it precludes lateral movement of the needle 102, thereby preventing needle 102 from jamming due to misalignment during operation.

Figure 20A:
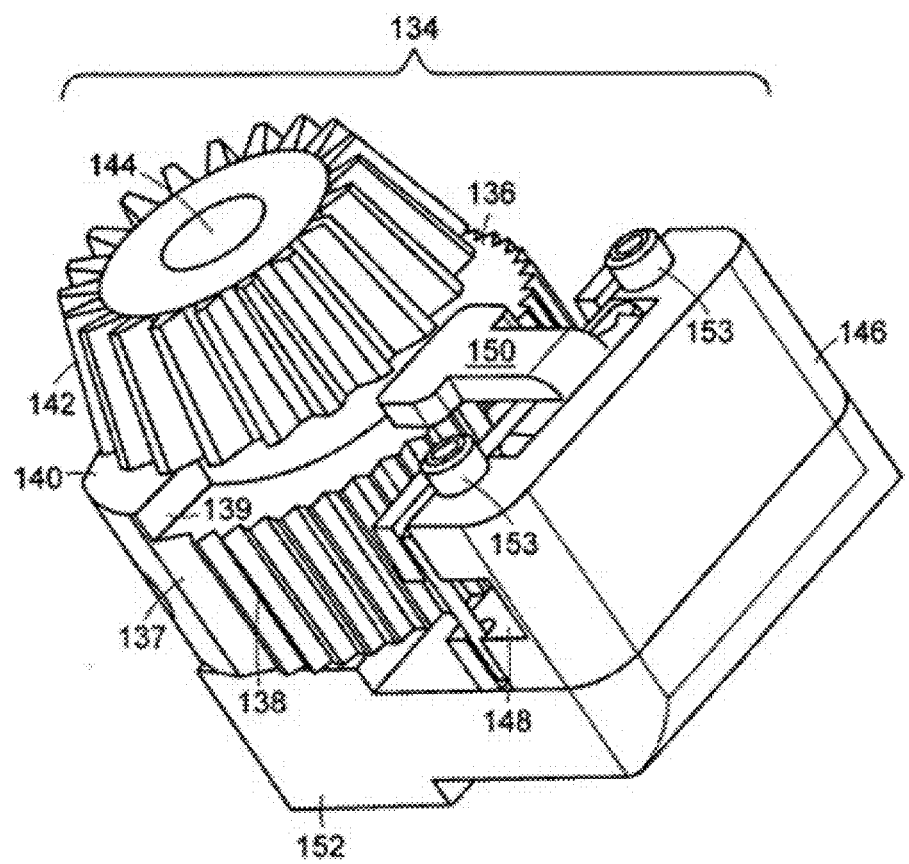
FIGS. 20A, 20B and 20C show a three-dimensional, a sectional and a cross-sectional view, respectively, of a ratchet assembly of the present disclosure that is driven by a drive shaft and activates a pusher arm upon device actuation.
Figure 20B:
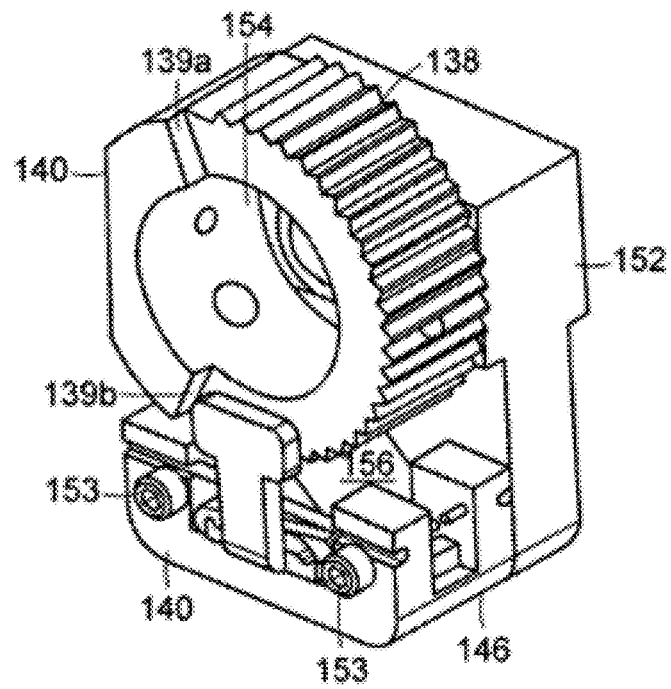
Figure 20C:
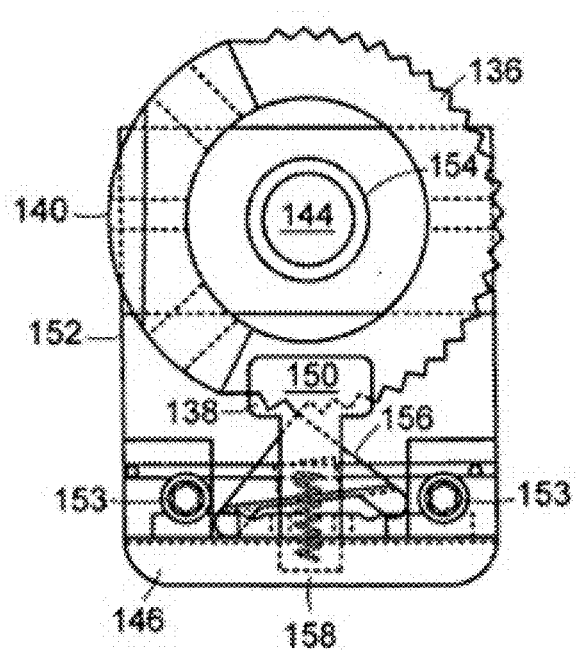

FIGS. 20A, 20B and 20C show the dimensional, sectional and transparent sectional views, respectively, of a ratchet assembly 134 of the present disclosure that is part of the drive mechanism for the suturing device 1. FIG. 20A shows the ratchet assembly 134 comprises a ratchet ring 136 with a predominantly arcuate outer surface segment 137 having a plurality of teeth 138, and an arcuate flat segment 140 that having a planar surface. The ratchet ring 136 includes a central circular bore (not shown) that fits slidably over and attaches immovably to a pinion gear 142 comprising a shaft 144. The ratchet ring 136 further comprises a plurality of wedged surfaces 139a and 139b that are proximal to the flat segment 140. The ratchet assembly 134 is mounted on a base 146 comprising a housing 148 that accommodates a pawl (hidden) that is activated by a coil spring (not shown) and a shuttle 150, that is attached to a support bracket 152 by a plurality of screws 153. FIG. 20B shows a detailed sectional view of the ratchet ring 136 comprising a circular bore 154 that is capable of slidably receiving and attaching to the shaft 144 of the pinion gear 142 (not shown). The ratchet ring 136 is mounted on the base 146 so that the teeth 138 of the ratchet ring 136 are interactively meshed with the pawl 156. The pawl 156 is activated by a coil spring (not shown) that exerts a positive pressure on the pawl 156 causing it to remain in intimate contact with the teeth 138 of the ratchet ring 136. The shuttle 150 is attached to the base so that it allows the ratchet ring 136 to rotate in a unidirectional (such as, for example, clockwise) until the circular movement is arrested by contact between the shuttle 150 and a first wedge 139a in the ratchet ring 136. Movement of the shuttle 150 after contacting the first wedge 139a permits the ratchet ring 136 to rotate in a direction opposite to the initial direction of rotation (such as, for example, counter-clockwise) until the movement is stopped by contact of shuttle 150 with the second wedge 139b. FIG. 20C shows a transparent sectional view of the ratchet ring 136 where the teeth 138 of the ratchet ring 136 are enmeshed with the pawl 156, which is maintained in intimate contact with the teeth 138 by a positive pressure exerted by the action of a coil spring 158.

The ratchet assembly 134 of the present disclosure may be suitably located within the handle 12 of the suturing device 1. In a preferred embodiment, the ratchet assembly 134 is located at the distal end 8 of the actuator handle 12, whereby the shaft 144 of the ratchet assembly 134 is a part of a shaft segment 10 that is terminally attached to a triggering mechanism of the suturing device 1. Activation of the suturing device 1 by actuating the triggering mechanism (not shown) via the trigger 16 in the actuator handle 12 causes the shaft 144 and the attached ratchet ring 136 and the pinion gear 142 in the ratchet mechanism 134 to rotate unidirectionally, the pinion gear 142 to drive the shaft segment 10 coupled to the driver arm 130 of the rear-drive mechanism in the pusher 9, which in turn, causes the engaged needle 102 to rotate in the same direction to effectuate penetration of incised tissue by the needle 102 pulling the suturing thread material with it. The rotation of the shaft 144 is arrested after travelling about 280° upon contact by a first wedge 139a with the shuttle 150, which in turn, terminates the first actuation step. The shuttle 150 then permits the shaft 144 with the attached ratchet ring 136 and the pinion gear 142 to rotate through an equal distance in the opposite direction until the movement is stopped once again by the contact by the shuttle 150 with the second wedge 139b. An advantage offered by the ratchet mechanism 134 of the present disclosure is that the actuation step of the suturing device 1 is pre-determined, that is, the ratchet assembly 134 prevents the user from performing an incomplete actuating event that could result in an improper or incomplete suture by causing the needle 102 to snag in the tissue. Furthermore, the ratchet assembly 134 is capable of operation by the trigger 16 in a manner independent of its orientation with respect to the trigger 16 and actuator handle 12, such as for example, when it is oriented in an upside down or sideways configuration.

The actuating means of the suturing device 1 of the present disclosure may comprise of a triggering mechanism that is known in the art, such as for example, the triggering mechanisms disclosed in U.S. Pat. Nos. 6,053,908 and 5,344,061, both of which are hereby incorporated by reference. Alternatively, the actuating means can be either a manually operable button or switch, or a mechanically operable by an automated electrical or a fuel driven device, such as for example, an electrical, electromagnetic or pneumatic motor powered by electrical, electromagnetic, compressed air, compressed gas, hydraulic, vacuum or hydrocarbon fuels.

To commence suturing, any embodiment of the suturing device 1 of the present disclosure is placed at the site of the wound or tissue incision such that it spans the wound or the two tissue segments created by the incision, following which it is actuated by operation of the actuator trigger 16 on the actuator handle 12. The detailed operation of the suturing device 1 of the present disclosure is described with reference to the preferred embodiment, and is equally applicable to all other embodiments of the disclosure described and contemplated herein. The pawl in the pusher mechanism of the suturing device 1 engages the notch 114 located radially rear edge proximal to the blunt end or "tail" of the suturing needle 102 and pushes the needle in a circular path in an arc spanning about 280°. The sharp, pointed end 108 of the needle 102 crosses the aperture 96 defined by the cartridge 84 and the cartridge holder 82, and penetrates the first tissue segment located within the aperture 96, traverses the tissue segment to penetrate the second tissue segment, and re-enters the device on the opposite side of the aperture 96. The pusher 9 then returns to its original location, whereupon the pawl engages the notch located radially rear edge 114 proximal to the sharp, pointed end of the needle 102. The needle 102 with the attached suturing material or thread is consequently pulled in a circular path through an arc of about 280°. The blunt end 110 of the needle 102 and the suturing material therefore, pass through the tissue segments and across the wound or incision so as to span the wound or incision. The needle 102 comes to rest at its original "home" position within the track in cartridge holder 82, having advanced through a complete circular arc of about 360°. The needle 102 including the sharp, pointed end 102 remains entirely contained within the cartridge 84. The suturing material or thread may then be cut and secured by an appropriate method, such as for example, by tying, or additional stitches may be placed along the entire wound or incision by repeating the aforementioned process. Every stitch, whether a single, interrupted stitch, or one of a series of continuous, running stitches may be placed in like manner. The suturing device 1 of the present disclosure, therefore, may be used to insert either a single stitch, or to insert a suture comprising a plurality of continuous stitches as a replacement method for a more tedious and time-consuming manual suturing process.

While a suturing device 1 having the separable suture cartridge 84 containing the suturing needle 102, a pusher 9 comprising a cartridge holder 82 with the support arms 80, a drive shaft assembly comprising the driver arm 130, and an actuator handle 12 comprising the actuating trigger 16 and drive mechanism has been described, the entire suturing device 1 can be designed as a single unit which may be either reusable or disposed in its entirety after a single use.

It will thus be seen that the examples set forth above among those made apparent from the preceding description are efficiently attained in the suturing device of the present disclosure. Also, since certain changes may be made in the above description without departing from the scope of the disclosure, it is intended that all matter contained in the above description or shown in the accompanying drawings shall be interpreted as illustrative, and not in a limiting sense.

What is claimed is:

1. A surgical suturing device, comprising:
   a needle defined at least in part by a leading end, a trailing end, an arced body between the leading and trailing ends, and at least one engagement surface formed into the needle;
   a length of suturing material connected to the needle;
   a needle rotation drive that reciprocates between a driven position and a returned position, the needle rotation drive being adapted to engage the at least one engagement surface of the needle to rotate the needle in a circular path in a first rotational direction along a circular needle track defined by a portion of the suturing device, wherein the leading end of the suturing needle is positioned within a protective housing of the surgical suturing device after a complete rotation of the suturing needle; and
   an anti-rotate pin that remains stationary with respect to the needle along the direction of the needle track as the needle is advanced in the first rotational direction by the needle rotation drive, the anti-rotate pin being configured to engage the needle to prevent the needle from rotating in a second rotational direction opposite to the first rotational direction to facilitate advancement of the needle along the needle track along the first direction in a plurality of drive strokes of the needle drive.

2. The surgical suturing device of claim 1, wherein the anti-rotate pin is positioned adjacent the driven position of the needle rotation drive.

3. The surgical suturing device of claim 1, wherein the anti-rotate pin extends into the needle's path of travel along the needle track.

4. The surgical suturing device of claim 1, wherein the needle is disposed in a removable cartridge that is removably attached to a cartridge holder assembly of the surgical suturing device.

5. The surgical suturing device of claim 4, wherein the cartridge holder assembly is configured to releasably engage the cartridge and to bring the needle rotation drive into operational contact with the suturing needle.

6. The surgical suturing device of claim 4, wherein the suturing material is also disposed within the cartridge.

7. The surgical suturing device of claim 6, wherein the cartridge further includes a suturing material dispenser containing the suturing material.

8. The suturing device of claim 7, wherein the cartridge further includes a thread management system for managing the dispensation of suturing material.

9. The surgical suturing device of claim 4, wherein the cartridge further includes at least one mounting clip wherein the cartridge is releasably engaged with the cartridge holder assembly having the needle rotation drive.

10. The surgical suturing device of claim 1, further comprising an actuator configured to engage the needle rotation drive to drive the suturing needle along the needle track.

11. The suturing device of claim 1, wherein the needle further defines an aperture adjacent to a blunt end of the needle for engaging the suturing material.

12. The suturing device of claim 1, wherein the needle is disposed within a disposable portion of the suturing device.

13. The suturing device of claim 12, wherein the disposable portion of the suturing device includes a removable cartridge.

14. A suturing device comprising:
a removable cartridge having a protective housing and a suturing needle having a pointed end and a second end, the suturing needle being configured to rotate about an axis, wherein the pointed end of the suturing needle is positioned within the protective housing after a complete rotation of the suturing needle about the axis;
a cartridge holder configured to releasably engage the protective housing of the removable cartridge; and
a needle rotation drive disposed at least partially within a housing, wherein the housing is positioned proximal of the cartridge holder, the needle rotation drive being configured to drive the needle about the axis, wherein engagement of the removable cartridge with the cartridge holder places the needle rotation drive into operable communication with the suturing needle.

15. The suturing device of claim 14, wherein the housing is reusable and the cartridge is disposable.

16. The suturing device of claim 15, wherein the suturing needle defines an opening in the second end thereof in the form of a cylindrical bore aligned axially with respect to the needle.

17. The suturing device of claim 16, wherein a leading end of a suturing material is inserted into the bore and restrained by mechanically crimping material of the needle onto the suturing material.

18. The suturing device of claim 17, wherein the needle is configured to be advanced along a circular needle track defined by the cartridge, across a gap in the needle track, and back into the needle track.

19. The suturing device of claim 18, wherein a center of rotation of the needle track that passes through the axis is unobstructed by the needle rotation drive.

20. The suturing device of claim 14, wherein the device is configured to push suture away from the circular needle track so the suture does not get pinched by the needle as the needle re-enters the circular needle track after passing across the gap.

21. The suturing device of claim 14, further comprising a deflectable anti-rotate pin that is configured to engage a surface of the needle to prevent the needle from backing up in the needle track.

22. The suturing device of claim 21, wherein the anti-rotate pin is configured to be engaged by the needle while the needle rotation drive reciprocates from a driven position to a home position.

23. The suturing device of claim 14, wherein the device defines a window near a distal end of the device that facilitates viewing of the suturing needle as it is advanced along the needle track.

24. The suturing device of claim 14, wherein the needle rotation drive is electrically automated.

25. The suturing device of claim 14, wherein the needle rotation drive includes an electric motor.

26. The suturing device of claim 14, wherein the needle rotation drive includes an electromagnetic motor.

27. The suturing device of claim 14, wherein the needle rotation drive includes a drive shaft.

28. The suturing device of claim 27, wherein the needle rotation drive further includes a flexible joint coupled to the drive shaft configured to transmit torque.

29. The suturing device of claim 14, further comprising a drive shaft configured to transmit torque through a flexible joint.

30. A suturing device comprising:
a needle rotation drive configured to drive an arcuate suturing needle having a first pointed end and a second end in a forward direction led by the first pointed end about a circular orbit;
a trigger operably connected to the needle rotation drive, wherein moving the trigger in a first direction actuates the needle drive through a drive stroke, and moving the trigger in a second direction actuates the needle drive through a return stroke; and
a ratchet preventing the needle rotation drive from progressing through the return stroke until the needle drive has been actuated through the drive stroke, wherein the ratchet includes an arcuate rack, the arcuate rack including a first end, a second end, and a length extending between the first and second ends, and a pawl configured to engage with the arcuate rack, and further wherein the pawl pivots between a first trailing oblique angle relative to the arcuate rack in the first direction and a second trailing oblique angle relative to the arcuate rack in the second direction.

31. The suturing device of claim 30, wherein the circular orbit lays in a plane that is generally perpendicular to a longitudinal axis of the suturing device.

32. The suturing device of claim 30, wherein the suturing device is configured to prevent the needle from moving in a backward direction opposite to the forward direction to maintain positional registration of the needle with respect to the needle rotation drive while the needle rotation drive is operating.

\* \* \* \* \*